United States Patent
Bujnicki et al.

(10) Patent No.: US 9,238,805 B2
(45) Date of Patent: Jan. 19, 2016

(54) DSRNA ENDORIBONUCLEASES

(71) Applicant: Miedzynarodowy Instytut Biologii Molekularnej I Komorkowej, Warsaw (PL)

(72) Inventors: Janusz Marek Bujnicki, Warsaw (PL); Krzysztof Jerzy Skowronek, Hornowek (PL); Dariusz Pianka, Warsaw (PL); Agata Agnieszka Sulej, Warsaw (PL)

(73) Assignee: Miedzynarodowy Instytut Biologii Molekulamej I Komorkowej, Warsaw (PL)

( * ) Notice: Subject to any disclaimer, the term of this patent is extended or adjusted under 35 U.S.C. 154(b) by 26 days.

(21) Appl. No.: 14/088,934

(22) Filed: Nov. 25, 2013

(65) Prior Publication Data

US 2014/0087427 A1   Mar. 27, 2014

Related U.S. Application Data

(63) Continuation-in-part of application No. PCT/PL2012/050020, filed on Jun. 7, 2012.

(60) Provisional application No. 61/494,574, filed on Jun. 8, 2011.

(30) Foreign Application Priority Data

Jun. 8, 2011   (PL) .......................................... 395178

(51) Int. Cl.
*C12P 19/34* (2006.01)
*C12N 9/22* (2006.01)

(52) U.S. Cl.
CPC . *C12N 9/22* (2013.01); *C12P 19/34* (2013.01); *C12Y 301/26003* (2013.01)

(58) Field of Classification Search
None
See application file for complete search history.

(56) References Cited

PUBLICATIONS

UNIPROT Accession No. D5RB71, Jul. 13, 2010, SubName: Full=Putative Uncharacterized Protein.
Gabriela Olmedo, et al., Mini-III, A Fourth Class of RNase III Catalyses Maturation of the Bacillus Subtilis 23S Ribosomal RNA, Molecular Microbiology (2008) vol. 68, No. 5, p. 1073-1076.
Yulia Redko, et al., Ribosomal Protein L3 Bound to 23S Precursor rRNA Stimulates Its Maturation by Mini-III Ribonuclease; Molecular Microbiology (2009) vol. 71, No. 5, p. 1145-1154.
Yulia Redko, et al., Mini-III, An Unusual Member of the RNase III Family of Enzymes, Catalyses 23S Ribosomal RNA MAturation in B. Subtilis, Molecular Microbiology (2008) vol. 68, No. 5, p. 1096-1106.

*Primary Examiner* — Tracy Vivlemore
*Assistant Examiner* — Kate Poliakova-Georgantas
(74) *Attorney, Agent, or Firm* — Vedder Price P.C.; Thomas J. Kowalski; Deborah L. Lu

(57) ABSTRACT

The invention relates to a new double-stranded RNA endoribonuclease, its derivative and/or variant, which has a loop locating in and interacting with the major groove of the double-stranded RNA, exhibiting sequence specific properties in the double-stranded RNA cleavage.

8 Claims, 7 Drawing Sheets

Fig. 2A-D
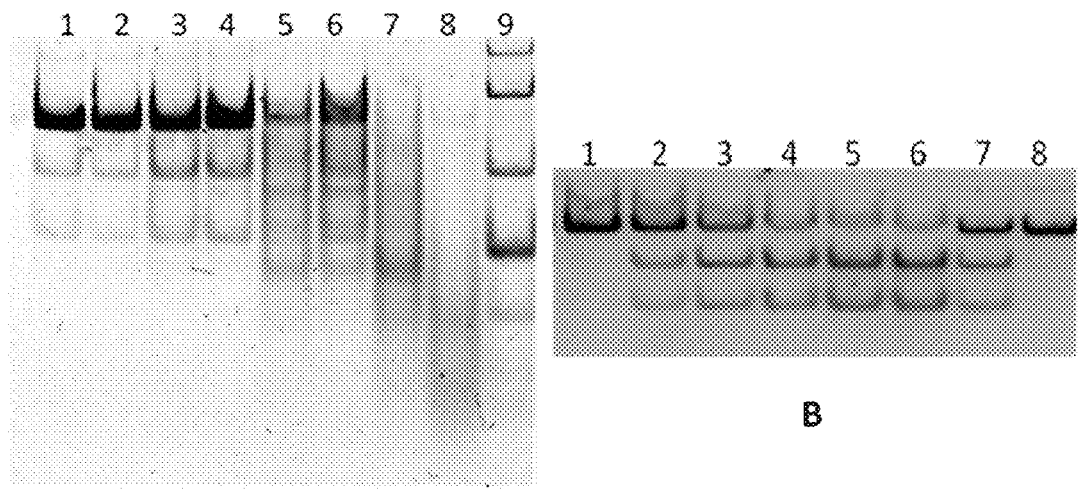
A
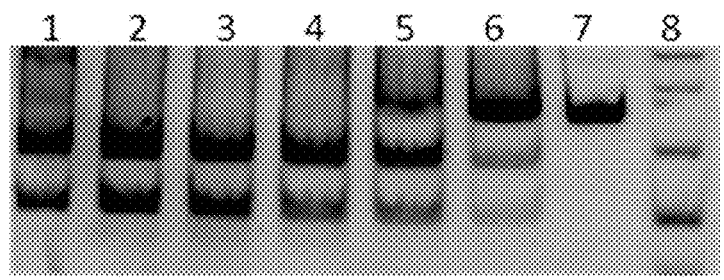
C
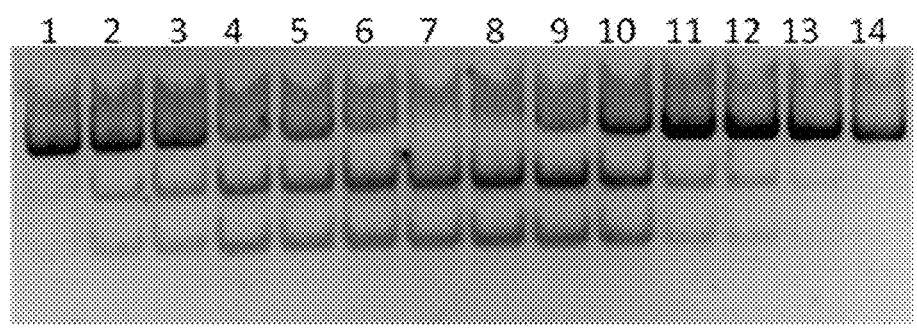
D

Fig 3A-B
A
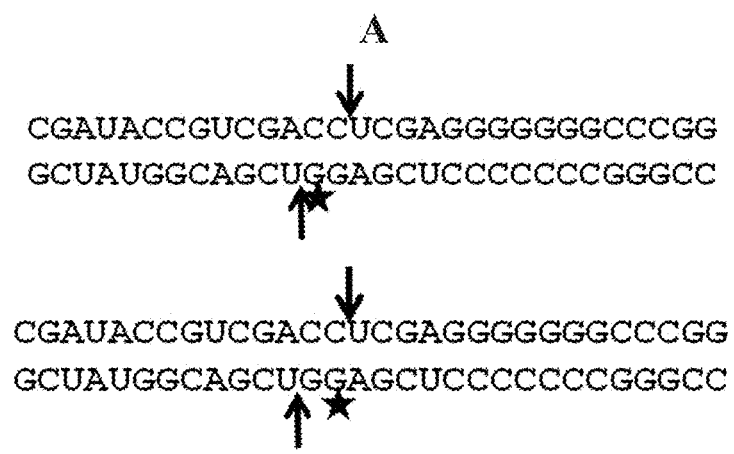
B
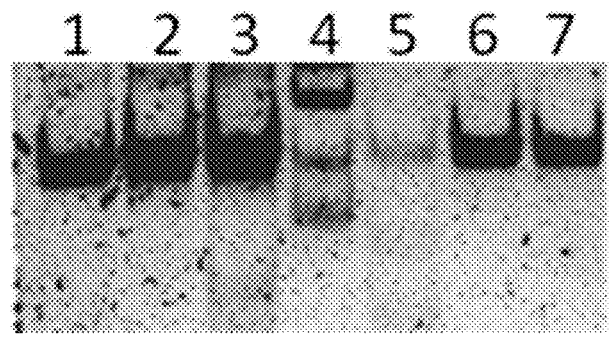

Fig. 6A-B
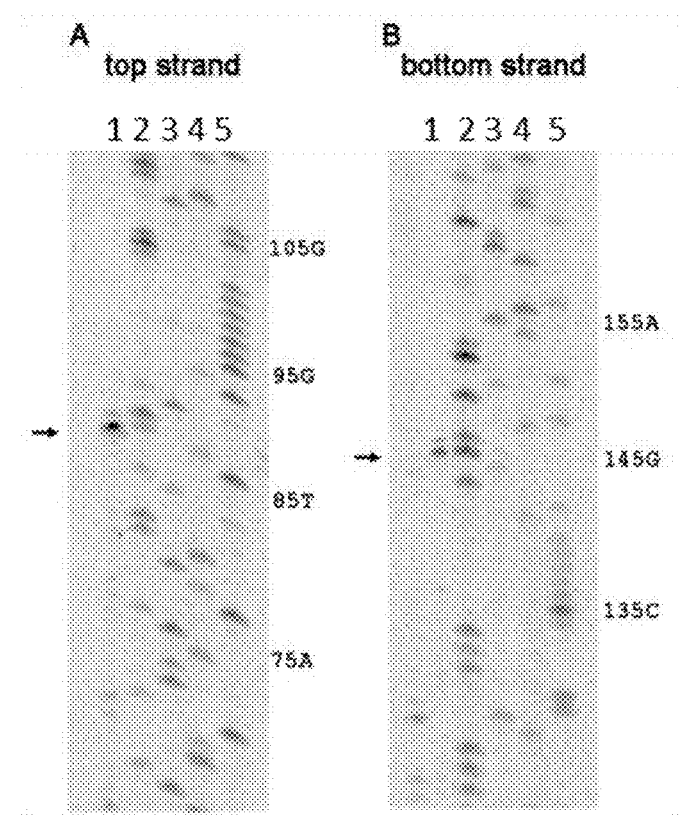

Fig. 7A-B
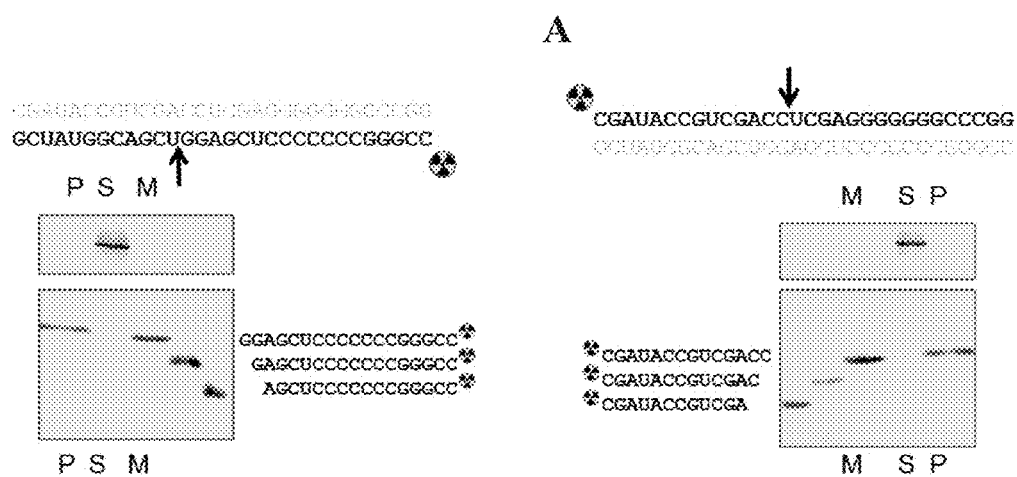
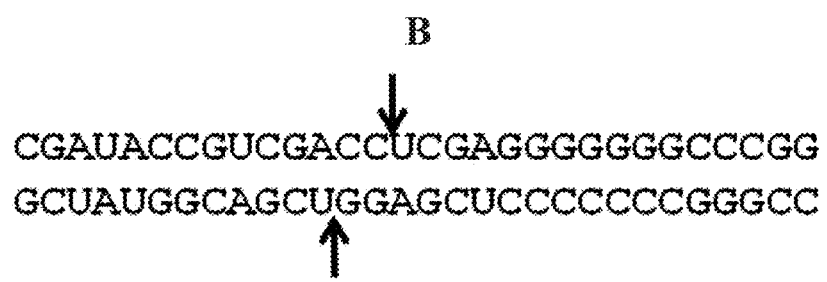
Fig. 8
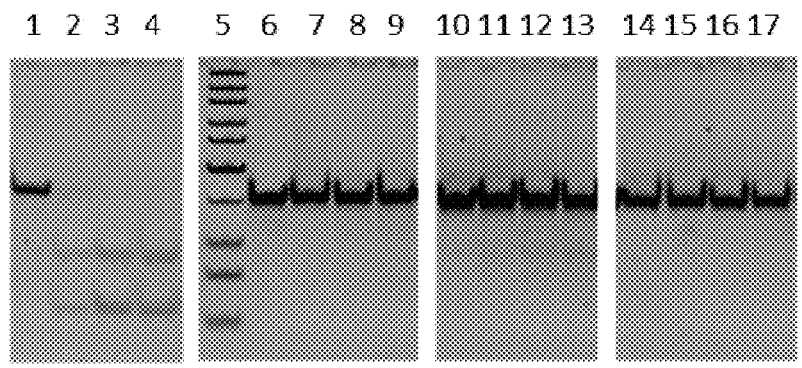

DSRNA ENDORIBONUCLEASES

RELATED APPLICATIONS AND INCORPORATION BY REFERENCE

This application is a continuation-in-part application of international patent application Serial No. PCT/PL2012/050020 filed 7 Jun. 2012, which published as PCT Publication No. WO 2012/169917 on 13 Dec. 2012, which claims benefit of Polish patent application Serial No. P.395178 filed 8 Jun. 2011 and U.S. provisional patent application Ser. No. 61/494,574 filed 8 Jun. 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Oct. 8, 2015, is named 46400.00.2002_SL.txt and is 44,243 bytes in size.

FIELD OF THE INVENTION

The subject of the invention is a double-stranded RNA (dsRNA) endoribonuclease exhibiting dsRNA sequence specific cleavage activity, the method of obtaining dsRNA endoribonuclease, the method obtaining dsRNA endoribonuclease derivative and/or a variant with altered sequence selectivity in dsRNA cleavage, genetic construct, the host cell, use of the gene encoding the dsRNA endoribonuclease to its creation, the kit and the enzyme exhibiting dsRNA endoribonucleolytic activity.

BACKGROUND OF THE INVENTION

One of the basic tools of molecular biology are proteins with a clearly defined activity, used for example in genetic engineering, diagnostics, medicine and industry in the manufacturing and processing of various products.

DNA restriction endonucleases are sequence dependent enzymes that recognize and cleave specific sequence of double-stranded DNA. There are also known enzymes that cleave RNA in a given sequence, however, such enzymes act on single-stranded sites in RNA. Examples of these enzymes include a phage protein RegB, which cleaves the single-stranded RNA in the middle of the sequence GGAG and Ribonuclease Y, which cleaves the single-stranded RNA in A or AU rich sequences. These enzymes require additional determinants for efficient cleavage, such as RNA secondary structure and in case of RegB the interaction with the ribosomal protein S1 (Lebars, I., et al., J Biol Chem (2001) 276, 13264-13272, Saida, F. et al., (2003) Nucleic Acids Res, 31, 2751-2758 and Shahbabian, K. et al., The EMBO Journal (2009) 28, 3523-3533). There were also attempts to change the specificity of Ribonuclease T1 and Ribonuclease MC1 (Hoschler, K. et al. J Mol Biol, (1999) 294, 1231-1238, Numata, T. et al., Biochemistry, (2003) 42, 5270-5278). In these two cases the enzyme variants were created in which their specificity has increased, from one to two nucleotides (Numata, T. et al., Biochemistry, (2003) 42, 5270-5278, Czaja, R. et al., Biochemistry, (2004) 43, 2854-2862; Struhalla, M. et al. Chembiochem, (2004) 5, 200-205). However, all these Ribonucleases still have a very limited sequence specificity which makes them unsuitable as molecular biology tools in applications similar to those of DNA restriction enzymes.

Ribonuclease III is an archetype of nucleases that cleave double-stranded RNA (dsRNA) and a founding member of the Ribonuclease III superfamily of proteins, which share an evolutionarily conserved catalytic domain. They are divided into four classes based on the occurrence of additional domains. Class 1, i.e., orthodox Ribonuclease III enzymes, have a double-stranded RNA binding domain (dsRBD) and a single Ribonuclease III domain. Class 2 and 3 enzymes are represented by Drosha and Dicer, respectively, which both comprise two Ribonuclease III domains along with a single dsRBD. In addition, enzymes belonging to class 2 possess additional domains, such as a polyproline domain and to class 3 a DExD helicase, DUF283 and PAZ domains. Class 4, called Mini III, includes enzymes that consist solely of the Ribonuclease III domain.

The natural substrate for the Mini III protein from *Bacillus subtilis* is 23S pre-rRNA, in which the 3' and 5' ends of the molecule are removed to yield the mature 23S rRNA. The cleavage site for this enzyme is known, however close to the cleavage site of double-stranded pre-rRNA one fragment of 23S pre-rRNA forms an irregular helix, which was speculated to be necessary for substrate recognition (Redko, Y. et al., Molecular Microbiology, (2008) 68 (5), 1096-1106). In addition, in vitro endoribonucleolytic activity of Mini III was shown to be stimulated by the ribosomal protein L3 bound to the 3' end of the 23S rRNA. There is indirect evidence that protein L3 enhances the cleavage of the substrate by changing the conformation of the RNA (Redko, Y. et al., Molecular Microbiology, (2009) 71 (5), 1145-1154).

There are no known enzymes for specific and defined dsRNA fragmentation with properties similar to the DNA restriction endonucleases or DNA nickases (JP 54059392-A, May 12, 1979). The dsRNA can be cleaved by endoribonucleases from Ribonuclease III family, but no details of Ribonuclease III-dsRNA interactions are known (Herskovitz, M. A. et al., Molecular Microbiology, (2000) 38 (5), 1027-1033). The criteria for site-specific binding and selective processing remain unclear (Dasgupta S. et al., Molecular Microbiology, (1998) 28 (3), 629-640). However, unspecific dsRNA endonucleases are used for generating short double-stranded RNA fragments (US 2006057590-A1, Mar. 16, 2006, NOVARTIS). Obtaining enzymes exhibiting sequence specificity in dsRNA cleavage will allow to develop all areas of RNA manipulation techniques, but also to develop new research methods, new applications of such enzymes and new technologies derived from them.

Citation or identification of any document in this application is not an admission that such document is available as prior art to the present invention.

SUMMARY OF THE INVENTION

In the light of the state-of-the-art, the object of the presented invention is to overcome the indicated disadvantages and to deliver the dsRNA endoribonuclease with high sequence specificity recognition and cleavage. The aim of the present invention is also to deliver methods of determining, isolation, selection, obtaining and preparation of such sequence-specific dsRNA endoribonucleases, and their improved variants.

The inventors have unexpectedly found out that an enzyme from the Ribonuclease III superfamily, which according to in silico modeling contains a loop that locates in and interacts with the major groove of the dsRNA helix, may have a preference for cleaving a particular dsRNA nucleotide sequence. The inventors have found that such preference depends only on the dsRNA sequence and is independent of the presence of irregular dsRNA helix structure and/or interaction with other proteins. The inventors have found out that the enzyme that belongs to the Ribonuclease III superfamily, which contains fragments of polypeptide chain that in in silico modeling forms a loop that locates in and interacts with dsRNA major groove, is able to perform specific and defined fragmentation of dsRNA with properties similar to the restriction endonucleases for DNA.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 2A-D. Shows the in vitro cleavage by endoribonuclease BSU from *Bacillus subtilis* performed to determine the optimal reaction conditions. A—effect of pH on the cleavage of 234 bp dsRNA. 1—pH 6.8, 2—pH 7.0, 3—pH 7.5, 4—pH 7.8, 5—pH 8.0, 6—pH 8.2, 7—pH 8.5, 8—pH 8.8, 9—dsRNA marker (New England Biolabs No: NO3635). B—the effect of temperature on the cleavage of 234 bp dsRNA. 1—15° C., 2—25° C. 3—30° C., 4—35° C., 5—40° C., 6—45° C., 7—50° C., 8—55° C. C—the effect of NaCl concentration on the cleavage of 234 bp dsRNA. 1—5 mM, 2—20 mM, 3—40 mM, 4—60 mM, 5—80 mM, 6—100 mM, 7—non cleaved substrate, 8—marker dsRNA (New England Biolabs No: NO3635); D—the effect of $Mg^{2+}$ ion concentration in mM in the cleavage of 234 bp dsRNA. 1—0.03, 2—0.05, 3—0.08, 4—0.1, 5—0.25, 6—0.5, 7—1, 8—2.5, 9—5, 10—7.5, 11—10, 12—12.5, 13—15, 14—17.5 mM $Mg^{2+}$.

FIG. 3A-B. Presents the sensitivity of endoribonuclease BSU to ribose methylation at guanosines near the cleavage site. (A) The sequences of two substrates: £SEQ ID NOS 20, 114, 20 and 114, respectively, in order of appearance): the cleavage site marked with arrows, ribose methylation marked with an asterisk (B) cleavage of substrates with and without ribose methylation. 1—30 bp non cleaved substrate without methylation, 2—30 bp non cleaved substrate with ribose methylation of the guanosine adjacent to the cleavage site, 3—30 bp non cleaved substrate with ribose methylation of guanosine in the second nucleotide adjacent to the cleavage site, 4—marker dsRNA (New England Biolabs No: NO3635), 5—30 bp substrate without methylation treated with endoribonuclease BSU, 6—30 bp substrate with ribose methylation of the guanosine residue adjacent to the cleavage site treated with endoribonuclease BSU, 7—30 bp substrate with ribose methylation of guanosine in the second nucleotide adjacent to the cleavage site.

FIG. 6A-B. (A): Identification of the endoribonuclease BSU cleavage site on the top strand of the 234 bp dsRNA. 1—mapping of the cleavage site on the top strand, 2—chain termination with ddCTP, 3—chain termination with ddTTP, 4—chain termination with ddATP, 5—chain termination with ddGTP. (B): Identification of the endoribonuclease BSU cleavage site on the bottom strand of the 234 bp dsRNA. 1—mapping of the cleavage site on the bottom strand, 2—chain termination with ddGTP, 3—chain termination with ddATP, 4—chain termination with ddTTP, 5—chain termination with ddCTP.

FIG. 7A-B. (A): Identification of the cleavage site in 30 bp dsRNA substrate with the sequence surrounding cleavage site in the 234 bp dsRNA. S—substrate, P—product, M—marker, FIG. 7A discloses SEQ ID NOS 20, 20, 114, 114, 115, 116, 118, 117, 119 and 120, respectively, in order of appearance. (B): Shows the geometry of the dsRNA cleavage by endoribonuclease BSU. FIG. 7B discloses SEQ ID NOS 20 and 114, respectively, in order of appearance.

FIG. 8. Cleavage of 30 bp dsRNA substrates. 1—30 bp substrate with preferred sequence, 2—30 bp substrate with preferred sequence treated with endoribonuclease BSU for 15 minutes, 3—30 bp substrate with preferred sequence treated with endoribonuclease BSU for 30 minutes, 4—30 bp substrate with preferred sequence treated with endoribonuclease BSU for 60 minutes, 5—DNA marker (Ultra Low Range, Fermentas no: SM1211), 6—30 bp substrate N1, 7—30 bp substrate N1 treated with endoribonuclease BSU for 15 minutes, 8—30 bp substrate N1 treated with endoribonuclease BSU for 30 minutes, 9—30 bp substrate N1 treated with endoribonuclease BSU for 60 minutes, 10—30 bp substrate N2, 11—30 bp substrate N2 treated with endoribonuclease BSU for 15 minutes, 12—30 bp substrate N2 treated with endoribonuclease BSU for 30 minutes, 13—30 bp substrate treated N2 with endoribonuclease BSU for 60 minutes, 14—30 bp substrate N3, 15—30 bp substrate N3 treated with endoribonuclease BSU for 15 minutes, 16—30 bp substrate N3 treated with endoribonuclease BSU for 30 minutes, 17—30 bp substrate N3 treated with endoribonuclease BSU for 60 minutes.

DETAILED DESCRIPTION OF THE INVENTION

Figure 1:
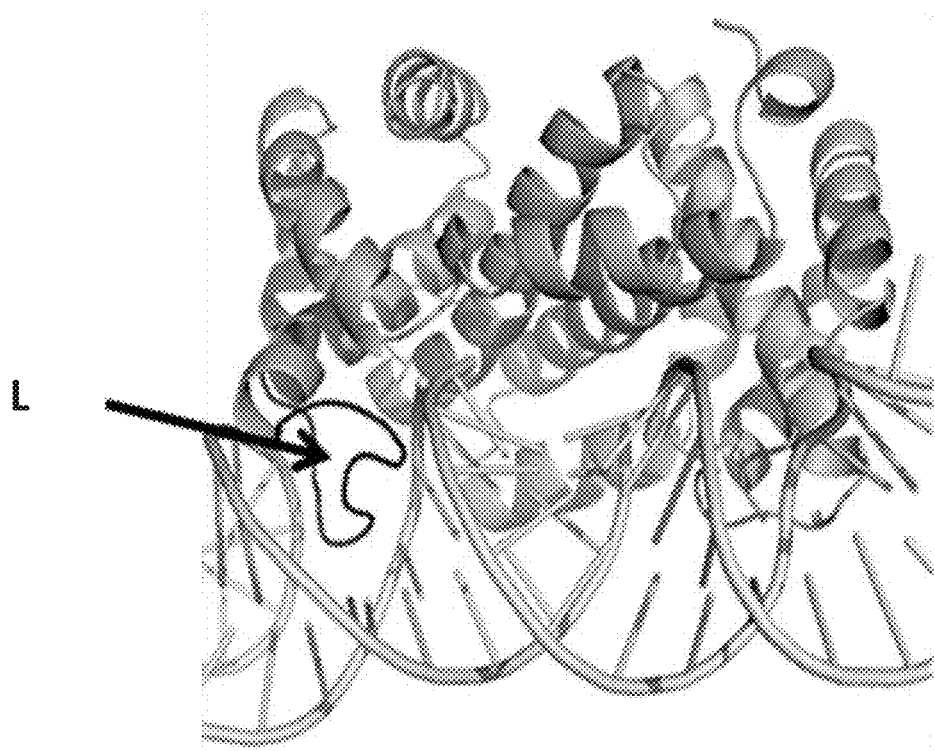
FIG. 1. A structural model of the complex of endoribonuclease Mini III from *Fusobacterium nucleatum* and the dsRNA. Loop (L) located in major groove of dsRNA marked by an arrow.

In one aspect the invention provides the dsRNA endoribonuclease exhibiting sequence specific properties in dsRNA cleavage, which has a loop that is locating in and interacting with a major groove of dsRNA and/or its derivative and/or variant exhibiting sequence specificity in dsRNA cleavage. In the preferred dsRNA endoribonuclease, its derivative and/or variant, the loop that is locating in and interacting with a major groove of dsRNA, has the amino acid sequence of dsRNA endoribonuclease, which corresponds to the loop locating in and interacting with a major groove of dsRNA in the model of structure of endoribonuclease Mini III in complex with dsRNA.

In the preferred dsRNA endoribonuclease, its derivative and/or variant the loop that is locating in and interacting with a major groove of dsRNA corresponds to the loop that is locating in and interacting with a major groove of dsRNA formed by a fragment of endoribonuclease FNU from *Fusobacterium nucleatum* as shown in SEQ ID NO:3 and/or by fragment of endoribonuclease BSU from *Bacillus subtilis* as shown in SEQ ID NO:4 and/or by fragment of endoribonuclease BCE from *Bacillus cereus* as shown in SEQ ID NO:5.

The dsRNA endoribonuclease, its derivative and/or variant preferably may comprise the sequence or a fragment of the amino acid sequence of dsRNA endoribonuclease BSU from *Bacillus subtilis* of SEQ ID NO:1, which shows sequence specificity in dsRNA cleavage and preferably contains an amino acid substitution D94R.

The dsRNA endoribonuclease, its derivative and/or variant also preferably may comprise the endoribonuclease FNU from *Fusobacterium nucleatum* or a fragment of endoribonuclease FNU from *Fusobacterium nucleatum*, which exhibits sequence specificity in dsRNA cleavage. The dsRNA endoribonuclease, its derivative and/or variant also preferably may comprise the endoribonuclease BCE from *Bacillus cereus* or a fragment of endoribonuclease BCE from *Bacillus cereus*, which exhibits sequence specificity in dsRNA cleavage.

In next aspect the invention relates to the method of obtaining dsRNA endoribonuclease exhibiting sequence specificity in dsRNA cleavage, which may comprise the following steps:
 a) selection of dsRNA endoribonuclease, its functional variant and/or derivative that may comprise an amino acid sequence forming a loop that is locating in and interacting with a major groove of dsRNA, wherein the loop is formed by the amino acid sequence of dsRNA endoribonuclease, which corresponds to the model of the loop locating in and interacting with a major groove of dsRNA determined by the three-dimensional model of the complex of Mini III endoribonuclease with dsRNA;
 b) cloning the gene or fragment thereof which encodes for a dsRNA endoribonuclease, its functional variant and/or derivative, which may comprise the sequence forming a loop that is locating in and interacting with a major groove of dsRNA.

The method of obtaining dsRNA endoribonuclease additionally preferably includes after step b) the next step c) expressing of the protein encoded by the gene or fragment thereof obtained in step b), and preferably after step c) it is also followed by step d) in which the sequence specificity of the isolated dsRNA endoribonuclease is determined.

In a preferred method of obtaining dsRNA endoribonuclease the loop that is locating in and interacting with a major groove of dsRNA corresponds to the amino acid sequence forming a loop that is locating in and interacting with a major groove of dsRNA formed by a fragment of dsRNA endoribonuclease FNU from *Fusobacterium nucleatum* as shown in SEQ ID NO:3 and/or by fragment of endoribonuclease BSU from *Bacillus subtilis* as shown in SEQ ID NO:4 and/or by fragment of endoribonuclease BCE from *Bacillus cereus* as shown in SEQ ID NO:5.

Moreover, in the next aspect the invention relates to the method of obtaining dsRNA endoribonuclease derivative and/or variant with altered sequence selectivity for sequence specific cleavage of dsRNA, which may comprise the following steps:
 a) introducing the change(s) in nucleotide sequence encoding the amino acid sequence corresponding to the loop located in the major groove of dsRNA for dsRNA endoribonuclease obtained in the method of obtaining dsRNA endoribonuclease of the invention, exhibiting sequence specificity in dsRNA cleavage;
 b) expression of the derivative and/or variant of dsRNA endoribonuclease from the nucleotide sequence obtained in the step a), and
 c) identification of the altered sequence specificity of derivative and/or variant of dsRNA endoribonuclease.

In such a preferred method the change in the selectivity of the derivative and/or variant of dsRNA endoribonuclease leads to a derivative and/or a variant with increased selectivity for nucleotide sequence in dsRNA cleavage.

The invention further relates to a method for producing dsRNA endoribonuclease, which includes the step of expressing dsRNA endoribonuclease, its derivative and/or a variant of the invention exhibiting sequence specificity in dsRNA cleavage.

The invention also relates to a genetic construct which may comprise a nucleotide sequence encoding a dsRNA endoribonuclease, a derivative thereof and/or a variant of the invention exhibiting sequence specificity in dsRNA cleavage.

A host cell which may comprise a genetic construct of the invention is also subject to the invention.

In the next aspect the invention relates to the use of the gene encoding the dsRNA endoribonuclease FNU from *Fusobacterium nucleatum* or fragment thereof and/or its functional variant and/or derivative to produce dsRNA endoribonucleases exhibiting sequence specific dsRNA cleavage. In a beneficial application the dsRNA endoribonuclease FNU from *Fusobacterium nucleatum*, its derivative and/or variant which may comprise the amino acid sequence shown in SEQ ID NO:3.

The invention also relates to the use of the gene encoding the dsRNA endoribonuclease BCE from *Bacillus cereus* or fragment thereof and/or its functional variant and/or derivative to produce dsRNA endoribonucleases exhibiting sequence specific dsRNA cleavage. Preferably the dsRNA endoribonuclease BCE from *Bacillus cereus*, its derivative and/or variant which may comprise the amino acid sequence of SEQ ID NO:5.

In next aspect the invention relates to the use of the gene encoding dsRNA endoribonuclease BSU from *Bacillus subtilis* shown in SEQ ID NO:1 or a fragment thereof and/or its functional variant and/or derivative to produce dsRNA endoribonuclease exhibiting sequence-specific dsRNA cleavage. Preferably the gene encoding dsRNA endoribonuclease BSU from *Bacillus subtilis*, its derivative and/or variant which may comprise the amino acid sequence shown in SEQ ID NO:1, even more preferably the gene encoding dsRNA endoribonuclease BSU from *Bacillus subtilis* which may comprise D94R substitution.

The invention also relates to the kit that may comprise dsRNA endoribonuclease, derivative and/or a variant thereof of the invention exhibiting sequence specificity in dsRNA cleavage. It may comprise dsRNA endoribonuclease FNU from *Fusobacterium nucleatum* and/or dsRNA endoribonuclease BCE from *Bacillus cereus* and/or dsRNA endoribonuclease BSU from *Bacillus subtilis* or a variant thereof which may comprise substitution D94R and/or their derivatives and variants exhibiting sequence specificity in dsRNA cleavage.

The invention also relates to enzyme of dsRNA endoribonuclease activity which may comprise a sequence or a fragment of the amino acid sequence from *Bacillus subtilis* shown in SEQ ID NO:1, which exhibits sequence specificity and cleaves the dsRNA within the consensus sequence (SEQ ID NOS: 111 and 121)

```
5' DACCUHD 3'

3' HUGGADH 5'
``` where H=A or C or U; D=A or G or U and its derivatives and/or variants that retain sequence specificity. The preferred enzyme and its derivatives and/or variants that retain sequence specificity in dsRNA cleavage and cut dsRNA within the consensus sequence (SEQ ID NOS: 112 and 122)

```
5' YGACCUCGNNG 3'

3' RCUGGAGCNNC 5'
``` where Y=C or U; R=A or G; N=G or A or U or C.

In the preferred enzyme and its derivatives and/or variants retaining the sequence specificity, the amino acid sequence may comprise substitution D94R of amino acid residue 94 presented in SEQ ID NO:1, its derivative and/or variant that retain sequence specificity.

The sequence specificity of dsRNA cleavage means the ability of dsRNA endoribonuclease to recognize and cut dsRNA depending only on its sequence and not on the existence of irregular helix structure in one or both strands dsRNA and/or interaction of other assisting proteins.

The term dsRNA endoribonuclease derivative and/or a variant as described herein, means proteins, polypeptides, peptides or recombinant proteins, polypeptides and peptides which may comprise the amino acid sequence identical or highly similar to the amino acid sequence of dsRNA endoribonuclease exhibiting sequence specific dsRNA cleavage, which has a loop that is locating in and is interacting with the major groove of dsRNA retaining the characteristic activity and sequence preference of dsRNA endoribonuclease. Such examples of derivatives and variants in the model of the structure will have a loop that corresponds to the loop locating in and interacting with the major groove of dsRNA in the structural model of the complex of endoribonuclease Mini III with dsRNA. In dsRNA endoribonuclease derivatives and/or variants exhibiting sequence specificity in dsRNA cleavage, the encoding sequences may be amended by the substitution, replacement, deletion or insertion, or other means in relation to the initial sequence. Such term should by analogy be likewise understood for the gene and/or derivative and/or a variant of the gene coding for dsRNA endoribonuclease with such characteristic.

The dsRNA endoribonucleases exhibiting sequence specificity, their derivatives and/or variants of the invention and their use permits the development of a whole new field of techniques for manipulating RNA, as well as to develop new research methods, new uses of such enzymes and new technologies derived from them. The dsRNA sequence-specific endoribonucleases, their derivatives and/or variants, for example, will be used in structural studies of RNA in order to understand the structure of RNA molecules and/or their modifications, in the generation of RNAi molecules, in particular siRNA, in diagnosis and treatment of viral diseases of plants and animals as well as in nanotechnology applications based on the so-called 'RNA tectonics'.

New sequence-specific endoribonucleases of the dsRNA, their derivatives and/or variants of the invention will be used for new biotechnological applications. There are known enzymes that cut single-stranded RNA in a sequence-dependent manner, but their activity depends not only on the sequence of the substrate, but also on its secondary structure, so in practice they are not very useful. New sequence-specific dsRNA endoribonucleases of dsRNA, their derivatives and/or variants of the invention do not have these drawbacks and can be used as common laboratory reagents such as restriction endonucleases used in molecular biology. In addition sequence-specific dsRNA endoribonucleases, their derivatives and/or variants also can be used in medicine, diagnostics and nanotechnology. For example, currently the direct sequencing of RNA in reverse transcription reaction or mass spectrometry is used most often to identify modifications in RNA structural studies, but in both cases analysis of large molecules (eg. rRNA or mRNA) is difficult. In these methods, RNA is fragmented to short RNA products or ribonucleotides by unspecific ribonucleases and the multitude of products makes the interpretation of the results difficult or even impossible. The application of new sequence-specific dsRNA endoribonucleases, their derivatives and/or variants allows the controlled cleavage of RNA molecule into recurring smaller fragments. Molecular weight and properties could be determined independently, allowing for the analysis of chemical modifications of ribonucleotides and RNA structural studies previously impossible or very difficult. Such studies of modifications and structures of RNA molecules will provide information on potential therapeutic targets, for example mechanisms of bacterial resistance to antibiotics. Application of new sequence-specific dsRNA endoribonucleases, their derivatives and/or variants allows for the development of technologies based on RNAi, short interfering dsRNA molecules. Sequence-specific dsRNA endoribonucleases, their derivatives and/or variants will be used in the siRNA methods and applications for gene silencing, for example, in medicine to treat cancer, metabolic diseases and neurodegenerative disorders. Currently, one of the strategies leading to obtain a short dsRNA is to treat the long dsRNA produced from a particular segment of DNA with Ribonuclease III from *Escherichia coli*. This enzyme cuts dsRNA nonspecifically, producing 18 to 25 base pairs fragments.

Short fragments are used for gene silencing. A completely new and unknown possibilities for the production of specific siRNA can be used by sequence-specific dsRNA endoribonucleases, their derivatives and/or variants of the invention enabling the defined pool of dsRNA fragments generation that efficiently silence expression of a particular gene without off target effects.

Sequence-specific dsRNA endoribonucleases, their derivatives and/or variants can be applied in the diagnosis and treatment of diseases caused bp dsRNA viruses. Such viruses belong to Reoviridae family in which three groups are pathogenic for humans. Currently to detect and identify those groups the reverse transcription reaction is used followed by PCR. Availability of sequence-specific dsRNA endoribonucleases, their derivatives and/or variants of the invention allows manipulation of dsRNA which significantly speeds up the diagnostics. Currently, treatment for rotavirus is highly ineffective. Sequence-specific dsRNA endoribonucleases, their derivatives and/or variants will be used as drugs for the treatment of rotavirus diseases by cleaving a specific viral genome, thereby preventing their further replication.

Sequence-specific dsRNA endoribonucleases, their derivatives and/or variants will also be used in nanotechnology, in particular in the "RNA tectonics" and the creation of nanostructures based on a given RNA sequence and structure.

Publications cited in the description and their references are entirely incorporated herein as reference.

In the following examples, unless otherwise indicated, standard materials and methods described in Sambrook J. et al., Molecular Cloning: A Laboratory Manual, 2nd edition. 1989. Cold Spring Harbor, N.Y. Cold Spring Harbor Laboratory Press are employed, or proceded in accordance with manufacturers' recommendations for specific materials and methods. Herein, unless otherwise indicated standard abbreviations for amino acids and nucleotides or ribonucleotides are used.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

In-Silico Indentification of Genes Encoding Proteins with Sequence-Dependent dsRNA Cleavage Activity Double-stranded RNA (dsRNA) cutting enzymes contain a ribonuclease III domain. This group includes Dicer and Drosha, which contain additional domains necessary for the functioning of these enzymes. Here are also classified bacterial dsRNA endoribonucleases, with additional dsRNA-binding domain and enzymes without any additional dsRNA-binding domains.

The records with numbers 2EZ6, 2GSL, 1U61 which are available in the PDB database (PDB database, present the spatial coordinates of experimentally solved structures of proteins and nucleic acids and their complexes: http://www.pdb.org), and were used to select proteins with a desired substrate specificity. 2EZ6 presents the structure of a ribonuclease III from Aquifex aeolicus having a dsRNA binding domain, together with the dsRNA substrate. 2GSL and 1U61 present structures of Mini III endoribonucleases (not possessing dsRNA binding domain) from *Fusobacterium nucleatum* and *Bacillus cereus* respectively. Using Swiss-PdbViewer (Guex, N., et al., Electrophoresis, (1997) 18, 2714-2723), the structure of the 2GSL protein was superimposed on the catalytic centre of the 2EZ6 protein in the complex with the RNA substrate. We found that the matched 2GSL endoribonuclease has a loop which locates in the major groove of dsRNA (see FIG. 1). The fragment of the polypeptide chain, which locates in the major groove, was identified after the removal of the original enzyme from the 2EZ6 complex and the creation of a new complex with the protein derived from 2GSL and RNA from 2EZ6. A structural model of the Mini III protein-RNA complex indicates that the loop encompasses the sequence AKNSNIKTFPRSCT (SEQ ID NO: 3) for *Fusobacterium nucleatum* Mini III protein (FNU), and the alignment of amino acid sequences of proteins similar to the Mini III protein indicates that the loop from *Bacillus subtilis* Mini III protein (BSU) has an amino acid sequence GRNAKSGTTPKNTD (SEQ ID NO: 4). The loop of each member of the Mini III family of proteins has a different amino acid sequence, however it is able to locate in the major groove of dsRNA and provides a basis for sequence-specific interactions of Mini III with dsRNA. The interactions of this loop in Mini III protein with the RNA may lead to sequence preferences of Mini III in the course of dsRNA cleavage.

This means that in particular the enzyme having a loop L in FIG. 1 located in the major groove of the dsRNA, Mini III, its functional variants, and other proteins with similar sequences, collectively described as "Mini III family of proteins" may have a nucleotide preference for dsRNA processing independent on the irregular helix dsRNA structure, which has been proven in the further described examples of the invention.

Therefore, for cloning and further enzyme engineering the genes were selected with open reading frames identified by sequencing of bacterial genomes of organisms *Bacillus subtilis, Fusobacterium nucleatum* and *Bacillus cereus*.

In the PDB database solved structures for FNU and BCE are available, therefore genes that encode them are also identified. As a result of the amino acid sequence alignment of proteins belonging to the Mini III family another enzyme BSU has also been selected for experimental studies. All proteins that belong to the Mini III family may have a preference for cleavage of particular sequences in dsRNA.

Example 2

Cloning of the Genes Designated in Example 1 from *Bacillus subtilis, Fusobacterium Nucleatum* and *Bacillus cereus* a) Preparation of Template DNA

Freeze-dried cells obtained from the ATCC strain collection were suspended in 500 μl LB, and then 1 μl of such suspension was added to the PCR reaction. Template DNA was obtained from strains of *Bacillus subtilis* available as ATCC 23857, *Fusobacterium nucleatum* available as ATCC 25586 and *Bacillus cereus* available as ATCC 1457 b) Vector Preparation 500 ng of vector pET28 (Novagen) was cleaved to completion with restriction enzymes NdeI and XhoI and products were separated on agarose gel. Product of size 5289 bp was recovered from the gel using a Gel Out kit (A & A Biotechnology) according to the manufacturer's protocol.

c) Isolation of PCR Products for Cloning of Genes Encoding Proteins with dsRNA Sequence-Dependent Activity PCR with 1 µl of DNA template obtained from an appropriate strain in point. a) was performed in Biorad thermocycler in 50 µl reaction mixture: 5 µl reaction buffer, 200 µM dNTP mix, 1 U Pfu polymerase (Fermentas) and 50 pmol of each primer: Bsu28f and Bsu28 for reaction with DNA from *B. subtilis*, Fnu28f and Fnu28r for reaction with DNA from *F. nucleatum*, Bce28f and Bce28r for reaction with the DNA of *B. cereus* (corresponding primer sequences are shown in Table 1). Control reactions were performed without a DNA template.

TABLE 1

| Organism | Primer name | Primer sequence | SEQ ID NO |
|---|---|---|---|
| Bacillus subtilis | Bsu28f | TACCCATATGCTTGA ATTTGATACG | 6 |
| | Bsu28r | TACTCGAGTCATGTT GCTGACTCATTTG | 7 |
| Fusobacterium nucleatum | Fnu28f | CCGCATATGGACAAT GTAGATTTTTCAAAG | 8 |
| | Fnu28r | GTGCTCGAGTCATCA TTCTCCCTTTATAAC TATATTTATAATTTT TTTTATTTC | 9 |
| Bacillus cereus | Bce28f | CCGCATATGGTCGAT GCAAAGCAATTAAAC AG | 10 |
| | Bce28r | TACTCGAGTCATGAT GATGTGCCCCCTTC | 11 |

PCR reaction was performed in standard conditions. The reaction mixture was separated on agarose gel and the fragments corresponding to the expected sizes 447 bp, 408 bp and 422 bp were isolated from the gel using a Gel Out kit (A & A Biotechnology) and were cleaved with NdeI and XhoI. Cleavage product was purified using the Clean Up kit (A & A Biotechnology) and ligated with the vector obtained in point. b). Ligation reaction was carried out with T4 DNA ligase (Fermentas). 100µ of chemocompetent bacteria *E. coli* strain Top10 (Invitrogen) was transformed with 10 µl of ligation mixture and the resulting transformants were selected on LB solid medium with kanamycin 50 µg ml. Plasmid DNA was isolated from selected colonies grown on 3 ml LB medium with kanamycin (50 µg/ml) using Plasmid Mini kit (A & A Biotechnology). The selection of transformants containing the recombinant plasmids was based on analysis of restriction maps, and then the samples were sequenced to confirm the correctness of the constructs (DNA Sequencing and Synthesis Service at the IBB PAS).

In this way the following plasmids were obtained:

pET28Bsu encoding wild-type sequence-specific dsRNA endoribonuclease from yazC gene of *B. subtilis* (BSU endoribonuclease amino acid sequence is presented in SEQ ID NO:2);

pET28Fnu encoding wild-type sequence-specific dsRNA endoribonuclease from *F. nucleatum* (endoribonuclease FNU);

pET28Bce encoding wild-type sequence-specific dsRNA endoribonuclease from *B. cereus* (endoribonuclease BCE).

Example 3

Expression and Purification of the Protein from the pET28Bsu Vector Encoding Wild-Type Enzyme from *Bacillus subtilis*

*Escherichia coli* strain ER2566 (New England Biolabs) was transformed with the pET28Bsu plasmid obtained in Example 2, transformations were performed as described in Example 2. Strains were selected on LB solid medium with 50 µg/ml kanamycin and 1% glucose. 25 ml of liquid LB medium with 50 µg/ml kanamycin and 1% glucose were inoculated with selected transformants and incubated for 16 hours at 37° C. Then 500 ml of liquid LB supplemented with 50 µg/ml kanamycin, was inoculated with 25 ml culture and incubated with shaking at 37° C. to $OD_{600}$~0.6 and then protein expression induced by adding IPTG to a 1 mM final concentration. Induction was carried out for 3 hours at 37° C. with shaking Cultures were centrifuged at 5000 g for 10 min at 4° C., resuspended in STE buffer and centrifuged again. Pellet was suspended in 20 ml of lysis solution (50 mM $NaPO_4$ pH 8.0, 300 mM NaCl, 10 mM imidazole, 10% glycerol, 1 mM PMSF, 10 mM BME, 0.1% Triton X-100), and then the bacterial cells were disintegrated using single pass through the Cell Disruptor (Constant Systems LTD) at pressure of 1360 atmospheres. Lysates were clarified by centrifugation in the ultracentrifuge at 20 000 g at 4° C. for 20 min. Protein was purified by affinity chromatography using polyhistidine tag present in the peptide chain.

Cell lysate was applied to a 7×1.5 cm column containing 5 ml Ni-NTA agarose (Sigma-Aldrich) equilibrated with four volumes of lysis buffer. The column was washed sequentially with the following buffers: lysis (50 ml), lysis supplemented with 2 M NaCl (50 ml), lysis supplemented with imidazole to a concentration of 20 mM (50 ml). The protein was eluted with lysis buffer supplemented with 250 mM imidazole and 1.5 ml fractions were collected. Flow rate was 0.9 ml/min and temperature 4° C. Fractions containing protein were combined, diluted to total volume of 50 ml in buffer R: 30 mM $NaPO_4$ pH 8.0, 30 mM NaCl, 10% glycerol, 10 mM BME.

In order to cut off polyhistidine tag 4 U thrombin (Sigma-Aldrich no. Catalog T4648) was added and the mixture was incubated at 4° C. overnight. To purify the protein from the thrombin and polyhistidine tag ion-exchange chromatography using SP Sepharose column (GE Healthcare) was used. Protein was eluted with a linear gradient of NaCl concentration from 30 mM to 1 M in buffer R, 1.5 ml fractions were collected. Fractions with protein were combined, diluted and frozen at −70° C.

Example 4

Preparation of dsRNA Substrates

Following substrates were used for determinations of endoribonuclease activity of expressed proteins:

a) bacteriophage Φ6 genome consisting of three segments: 2948 bp (S), 4063 bp (M) and 6374 bp (L). This substrate contains 46 consensus cleavage sequences, but does not contain any preferred cleavage sequence. The dsRNA of bacteriophage Φ6 was purchased from Finnzymes.

b) in vitro synthesized dsRNA substrate, length 234 bp. This substrate contains single preferred cleavage site.

For the synthesis of 234 bp dsRNA pKSII plasmid with the modified DNA sequence downstream the T7 promoter site (sequence of modified pKSII is presented in SEQ ID NO:2) and primers:

```
bsuRNAf
                                    (SEQ ID NO: 12)
5'GCGCGTAATACGACTCACTATAGGG 3',
and bsuRNAr
                                    (SEQ ID NO: 13)
5'GGAAAAAAATCCGGCTCGTATGTTGTG 3'
were used.
```

Synthesis was performed with the Replicator RNAi Kit (Finnzymes, according to the manufacturer's protocol).

c) short 18, 20, 22 and 30 bp dsRNAs.

Single-stranded RNA oligonucleotides were synthesized at Metabion. Complementary oligonucleotides (1.5 nmol each) were mixed in a 1:1 ratio. 30 µl mixture was heated to 95° C., then cooled for 2 hours to room temperature. Oligonucleotide sequences are listed below:

```
                                    (SEQ ID NO: 14)
18F - 5'ACCGUCGACCUCGAGGGG 3'

(SEQ ID NO: 15)
18R - 5'CCCCUCGAGGUCGACGGU 3'

(SEQ ID NO: 16)
20F - 5'AUACCGUCGACCUCGAGGGG 3'

(SEQ ID NO: 17)
20R - 5'CCCCUCGAGGUCGACGGUAU 3'

(SEQ ID NO: 18)
22F - 5'AUACCGUCGACCUCGAGGGGGG 3'

(SEQ ID NO: 19)
22R - 5'CCCCCCUCGAGGUCGACGGUAU 3'

(SEQ ID NO: 20)
30F - 5'CGAUACCGUCGACCUCGAGGGGGGGCCCGG 3'

(SEQ ID NO: 21)
30R - 5'CCGGGCCCCCCCUCGUGGUCGACGGUAUCG 3'

(SEQ ID NO: 22)
30N1F - 5'UCGAGUUGCCGGUUGCUGUGAUGGCCGUUC 3'

(SEQ ID NO: 23)
30N1R - 5'GAACGGCCAUCACAGCAACCGGCAACUCGA 3'

(SEQ ID NO: 24)
30N2F - 5'CCACUCUUAGAUACCCGAUUCCCCUGUUUC 3'

(SEQ ID NO: 25)
30N2R - 5'GAAACAGGGGAAUCGGGUAUCUAAGAGUGG 3'

(SEQ ID NO: 26)
30N3F - 5'UCUGAUGGGCGCUACCGGUUCCGGUAAGUC 3'

(SEQ ID NO: 27)
30N3R - 5'GACUUACCGGAACCGGUAGCGCCCAUCAGA 3'
```

Example 5

Cleavage of the dsRNA Substrates by the Produced Enzymes

The reactions of substrate cleavage by the enzyme were carried out at 37° C. for 1 hour. 15 µl reaction mixtures contained 4 pmol of corresponding enzyme prepared according to example 3, 2 pmol of a substrate obtained according to Example 4, 1.5 µl reaction buffer (100 mM Tris-HCl pH 7.5, 50 mM NaCl, 10 mM MgCl 2, 1 mg/ml BSA). Products were separated in a standard agarose gel electrophoresis or polyacrylamide gel electrophoresis (6% polyacrylamide, TBE: 135 mM Tris-HCl, 45 mM boric acid, 2.5 mM EDTA). After electrophoresis the gels were stained with ethidium bromide for 10 minutes and the products were visualized using UV light.

Example 6

Determination of Cleavage Sites in dsRNA a) Primer Labeling

RTr primer with sequence 5'GAAACAGCTATGAC-CATGA 3' (SEQ ID NO:28) and RTf primer with sequence 5'GATCCCCCACAATCCTGTC 3' (SEQ ID NO:29) were radioactively labeled using [γ-33 P] ATP. Reactions (10 µl volume) containing 10 pmol of primer, 1 µl reaction buffer, 10 µCi [γ-33 P] ATP and 1 U T4 polynucleotide kinase (Fermentas) were carried out at 37° C. for 30 minutes.

b) Identification of the Cleavage Site on 234 bp dsRNA

It was shown that in the 234 bp dsRNA substrate obtained in Example 4b, there is only one cleavage site for endoribonuclease $BSU^{WT}$. 234 bp dsRNA was cleaved as described in Example 5 using the endoribonuclease $BSU^{WT}$. Then, the 90 bp and 144 bp products were isolated from the gel. Cleavage site was located using the reverse transcription reaction. 0.1 µg of each product was mixed with 1 pmol of radioactively labeled primers from Example 6a. These 12.5 µl mixtures were incubated at 95° C. for 5 minutes. Then the mixtures were supplemented with 4 µl reaction buffer (Fermentas), 20 U Ribonuclease inhibitor RiboLock (Fermentas), 2 µl 10 mM dNTP, 10 U AMV reverse transcriptase (Fermentas) and reactions were carried out at 45° C. for 60 min. In parallel sequencing was performed with the same primers and template using a reverse transcription reaction described above, except that in addition to the reaction mixture ddATP, ddCTP, ddGTP, or ddUTP in a ratio of 1:100 to the dNTP were added (to separate reactions). The reaction products were separated on 6% denaturing polyacrylamide gel (6% polyacrylamide, TBE: 135 mM Tris-HCl, 45 mM boric acid, 2.5 mM EDTA, 8M urea) and subjected to 16 hours exposure to Storage Phosphor Screen (GE Healthcare), and visualized using a Storm scanner (GE Healthcare). The cleavage site between nucleotide position 90 and 91 on the top strand of the dsRNA (see FIG. 6A, Table 2) and between 146 and 147 on the bottom strand was located (see FIG. 6B).

c) Identification of Cleavage Sites on Both Strands of dsRNA

To determine the cleavage sites on both strands 30 bp dsRNA substrate was prepared by annealing RNA oligonucleotides 30F and 30R. The 5' end of one strand was labeled with [γ-33P]ATP and T4 polynucleotide kinase and annealed with a non-labeled complementary oligonucleotide. Single-stranded RNA molecules with a cleavage site sequence derived from 234 bp dsRNA were synthesized (Metabion). Substrates were cleaved with endoribonuclease $BSU^{WT}$. Products were separated on 15% denaturing polyacrylamide gel (15% polyacrylamide, TBE: 135 mM Tris-HCl, 45 mM boric acid, 2.5 mM EDTA, 8M urea). Visualization of the products was done as in Example 6b. Results are shown in FIG. 7. Exact cleavage site and geometry of the generated ends were determined. Endoribonuclease $BSU^{WT}$ generates 2 nucleotide 3' overhangs (FIG. 7b).

TABLE 2

Identified cleavage site - sequence recognized and cut in the 234 bp dsRNA substrate by endoribonuclease BSU$^{WT}$

| Nucleotide position in the 234 bp dsRNA substrate | - | - | 83 | 84 | 85 | 86 | 87 | 88 | 89 | 90 | 91 | 92 | 93 | 94 | 95 | 96 | - | - | |
|---|---|---|---|---|---|---|---|---|---|---|---|---|---|---|---|---|---|---|---|
| Nucleotide sequence 234 bp dsRNA substrate | | | C | G | U | C | G | A | C | C | U | C | G | A | G | G | | | Residues 83-96 of SEQ ID NO: 30 |

It was shown that endoribonuclease BSU$^{WT}$ from *Bacillus subtilis* specifically recognizes and cuts single site in 234 bp dsRNA.

Example 7

Figure 4:
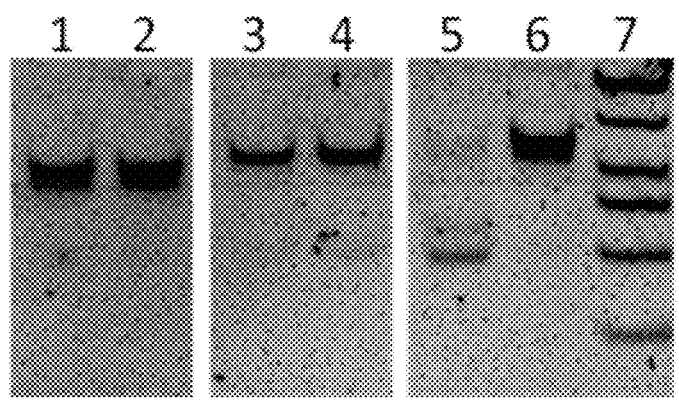
FIG. 4. Determination of minimum substrate length for endoribonuclease BSU. 1—18 bp substrate treated with endoribonuclease BSU, 2—untreated 18 bp substrate, 3—20 bp substrate treated with endoribonuclease BSU, 4—untreated 20 bp substrate, 5—22 bp substrate treated with endoribonuclease BSU, 6—untreated 22-bp substrate, 6—DNA marker (Ultra Low Range, Fermentas no: SM1211).

Determination of the Optimal Reaction Conditions for In Vitro Cleavage of dsRNA Substrates by the Produced Enzymes a) Impact of the Condition Changes on the Enzymatic Activity of Endoribonuclease BSU$^{WT}$ The influence of various factors on the enzymatic activity of the wild-type endoribonuclease BSU was examined. Optimum conditions were determined in in vitro cleavage, in various temperatures, pH, NaCl concentrations and Mg$^{2+}$ ion concentrations. Cleavage reaction was carried out as in Example 5, by changing only the parameter tested. Effect of pH on the cleavage of substrate was tested at pH values: 6.8, 7.0, 7.5, 7.8, 8.0, 8.2, 8.5, 8.8. It is shown that the best cleavage of 234 bp dsRNA substrate is obtained at pH 6.8, 7.0, 7.5, 7.8 (FIG. 3A). Effect of temperature on activity was tested at temperatures: 15° C., 25° C., 30° C., 35° C., 40° C., 45° C., 50° C., 55° C. The optimal temperature for the cleavage was between 35° C. and 45° C. (FIG. 2B). Outside this temperature range the substrate is cut at a slower rate. Effect of ion concentration was studied at NaCl concentrations of 5, 20, 40, 60, 80, 100 mM. Optimum for enzyme activity ranges from 5 to 60 mM of sodium chloride (FIG. 2C). Cutting efficiency of the substrate decreases at higher concentrations of salt. Effect of Mg$^{2+}$ ion concentration was tested at the values: 0.03, 0.05, 0.08, 0.1, 0.25, 0.5, 1, 2.5, 5, 7.5, 10, 12.5; 15, and 17.5 mM. Optimum Mg$^{2+}$ ions concentration in the reaction mixture is 1 to 2.5 mM (FIG. 2D). Outside this range the substrate is cut at a slower rate.

b) The Effect of Ribose Methylation in the Vicinity of the Endoribonuclease BSU$^{WT}$ Cleavage Site Sensitivity of the endoribonuclease BSU$^{WT}$ to ribose methylation in the vicinity of the cleavage site was analyzed. 30 bp dsRNA substrates with ribose methylation of two guanosines were tested (FIG. 3A). Cleavage reaction was carried out as in Example 5. Two substrates with the methylated guanosine ribose are not cut (FIG. 3B). The enzyme is sensitive to ribose methylation of two guanosine residues, which are close to the cleavage site.

c) Identification of a Minimum Length Substrate for dsRNA Cleavage by the Endoribonuclease BSU$^{WT}$ Minimum dsRNA substrate for endoribonuclease BSU$^{WT}$ was identified. For this purpose 18, 20 and 22 bp substrates were examined. Endoribonuclease BSU$^{WT}$ is able to cut dsRNA with a length of 22 base pairs (FIG. 4). Shorter substrates are not cut.

Example 8

Construction of the Substrate Libraries with Substitutions and Production of the dsRNA Substrates a) Construction of the Substrate Libraries with Substitutions 14 single position substitution libraries were constructed in the fragment of nucleic acid which may comprise a cleavage site for the 234 bp substrate (Table 2). In order to introduce substitutions the pairs of primers were designed with mutation at a given position. One of the pair of primers contains the appropriate substitution. The template for PCR was a modified plasmid pKSII shown in SEQ ID NO:2. PCR reaction with each primer pair was carried out according to the method and conditions described in Example 2. The sequences of primers used to produce substitute libraries are presented in Table 3 below.

TABLE 3

Shows the number of positions, sequences and the names of primer pairs used in the substitution library creation (where H = A or C or U; D = A or G or U; B = C or G or U; V = A or C or G)

| Library number | Position of the nucleotide substitution | Primer name | Primer sequence | SEQ ID NO |
|---|---|---|---|---|
| 1 | 83 | Subf | CTCGAGGGGGGGCCCGGTA | SEQ ID NO: 31 |
| | | Sub83r | GTCGACHGTATCGATAAGCTTG | SEQ ID NO: 32 |
| 2 | 84 | Subf | CTCGAGGGGGGGCCCGGTA | SEQ ID NO: 31 |
| | | Sub84r | GTCGADGGTATCGATAAGCTTG | SEQ ID NO: 33 |

TABLE 3-continued

Shows the number of positions, sequences and the names
of primer pairs used in the substitution library creation
(where H = A or C or U; D = A or G or U; B = C or G or U;
V = A or C or G)

| Library number | Position of the nucleotide substitution | Primer name | Primer sequence | SEQ ID NO |
|---|---|---|---|---|
| 3 | 85 | Subf | CTCGAGGGGGGCCCGGTA | SEQ ID NO: 31 |
|  |  | Sub85r | GTCGBCGGTATCGATAAGCTTG | SEQ ID NO: 34 |
| 4 | 86 | Subf | CTCGAGGGGGGCCCGGTA | SEQ ID NO: 31 |
|  |  | Sub86r | GTCHACGGTATCGATAAGCTTG | SEQ ID NO: 35 |
| 5 | 87 | Subf | CTCGAGGGGGGCCCGGTA | SEQ ID NO: 31 |
|  |  | Sub87r | GTDGACGGTATCGATAAGCTTG | SEQ ID NO: 36 |
| 6 | 88 | Subf | CTCGAGGGGGGCCCGGTA | SEQ ID NO: 31 |
|  |  | Sub88r | GVCGACGGTATCGATAAGCTTG | SEQ ID NO: 37 |
| 7 | 89 | Subf | CTCGAGGGGGGCCCGGTA | SEQ ID NO: 31 |
|  |  | Sub89r | HTCGACGGTATCGATAAGCTTG | SEQ ID NO: 38 |
| 8 | 90 | Sub90f | DTCGAGGGGGGCCCGGTA | SEQ ID NO: 40 |
|  |  | Subr | GTCGACGGTATCGATAAGCTTG | SEQ ID NO: 39 |
| 9 | 91 | Sub91f | CVCGAGGGGGGCCCGGTA | SEQ ID NO: 41 |
|  |  | Subr | GTCGACGGTATCGATAAGCTTG | SEQ ID NO: 39 |
| 10 | 92 | Sub92f | CTDGAGGGGGGCCCGGTA | SEQ ID NO: 42 |
|  |  | Subr | GTCGACGGTATCGATAAGCTTG | SEQ ID NO: 39 |
| 11 | 93 | Sub93f | CTCHAGGGGGGCCCGGTA | SEQ ID NO: 43 |
|  |  | Subr | GTCGACGGTATCGATAAGCTTG | SEQ ID NO: 39 |
| 12 | 94 | Sub94f | CTCGBGGGGGGCCCGGTA | SEQ ID NO: 44 |
|  |  | Subr | GTCGACGGTATCGATAAGCTTG | SEQ ID NO: 39 |
| 13 | 95 | Sub95f | CTCGAHGGGGGCCCGGTA | SEQ ID NO: 45 |
|  |  | Subr | GTCGACGGTATCGATAAGCTTG | SEQ ID NO: 39 |
| 14 | 96 | Sub96f | CTCGAGHGGGGCCCGGTA | SEQ ID NO: 46 |
|  |  | Subr | GTCGACGGTATCGATAAGCTTG | SEQ ID NO: 39 |

PCR products were separated on agarose gel and then isolated as described in Example 2. The isolated products were phosphorylated and ligated. The reaction was carried out at 37° C. for 1 hour. The 20 µl ligation mixture contained 100 ng of PCR product, 2 µl reaction buffer, 10 mM ATP, 1 U T4 polynucleotide kinase and 1 U T4 DNA ligase. *E. coli* TOP10 cells were transformed with 10 µl of ligation mixture as described in Example 1. Then cells were plated on the LB petri dish with 100 µg/ml ampicillin. To search for clones with introduced substitutions constructs the sequence was analyzed by sequencing as described in Example 2. Plasmids with appropriate substitution introduced were numbered as library from 1 to 14, which served as templates to synthesize dsRNA.

b) In Vitro Synthesis of dsRNA Substrates from Substitution Library Obtained in Point a)

Selected constructs from substitution library identified as a number from 1 to 14 were used as templates to synthesize dsRNA using primers bsuRNAf and bsuRNAr described in Example 4b.

Example 9

Determination of the Preferred Cleavage Sequence for the Endoribonuclease $BSU^{WT}$ The preferred sequence was determined using substrates synthesized in Example 8b. The cleavage reaction was carried out as in Example 5 using endoribonuclease $BSU^{WT}$ prepared in accordance with the Example 3. The following Table 4 shows the determined sequence preference for endoribonuclease $BSU^{WT}$.

TABLE 4

Cleavage of 234 bp dsRNA substitution libraries at positions from 83 to 96.

| No |  |  | 83 | 84 | 85 | 86 | 87 | 88 | 89 | 90 | 91 | 92 | 93 | 94 | 95 | 96 |  |  | SEQ ID NO |
|---|---|---|---|---|---|---|---|---|---|---|---|---|---|---|---|---|---|---|---|
| Sequence of the initial substrate |  |  | C | G | U | C | G | A | C | C | U | C | G | A | G | G |  |  | Residues 83-96 of SEQ ID NO: 30 |
|  |  |  |  |  |  |  |  |  |  |  |  |  |  |  |  |  |  |  |  |
| G |  |  |  |  | G | G | G | g | G | - | - | - | - | G | G | G |  |  | substitutions |
| A |  |  |  |  | A | A | A | a | a | A | - | - | - | A | a | A | A |  | present in |

TABLE 4-continued

Cleavage of 234 bp dsRNA substitution libraries at positions from 83 to 96.

| No | - | - | 83 | 84 | 85 | 86 | 87 | 88 | 89 | 90 | 91 | 92 | 93 | 94 | 95 | 96 | - | - | SEQ ID NO |
|---|---|---|---|---|---|---|---|---|---|---|---|---|---|---|---|---|---|---|---|
| Sequence of the initial substrate | | | C | G | U | C | G | A | C | C | U | C | G | A | G | G | | | Residues 83-96 of SEQ ID NO: 30 |
| U | | | U | U | U | U | u | - | - | - | U | U | u | U | U | U | | | SEQ ID NOS 47 to 88 |
| C | | | c | c | c | c | - | - | c | c | - | c | - | c | c | c | | | |
| Preferred sequence | | | N | N | N | Y | G | A | C | C | U | C | G | N | N | G | | | SEQ ID NO: 113 |

"uppercase"- dsRNA cleavage efficiency as for the initial substrate, "lowercase"- impared dsRNA cleavage; "-"- no cleavage Endoribonuclease BSU$^{WT}$ during the cleavage of dsRNA has shown sequence preference. The preferred cleavage sequence can be written as shown below in Table 5.

TABLE 5

The preferred cleavage sequence (SEQ ID NO: 112) of the dsRNA for the endoribonuclease BSU$^{WT}$. Cleavage site indicated by arrows. (where Y = C or U; R = A or G; N = G or A or U or C)

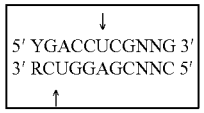

```
       ↓
5' YGACCUCGNNG 3'
3' RCUGGAGCNNC 5'
       ↑
```

However, endoribonuclease BSU$^{WT}$ is also able to cut the dsRNA substrates that have a consensus sequence as shown in the following Table 6.

TABLE 6

The consensus sequence (SEQ ID NO: 111) of endoribonuclease BSU$^{WT}$ dsRNA substrate. Cleavage site indicated by arrows. (where H = A or C or U; D = A or G or U)

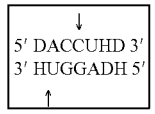

```
     ↓
5' DACCUHD 3'
3' HUGGADH 5'
     ↑
```

Endoribonuclease BSU$^{WT}$ generates sticky ends with 3' 2 nucleotide overhangs in dsRNA.

Example 10

Creation of the Endoribonuclease BSU Variants

Recombinant coding the wt sequence of endoribonuclease BSU$^{WT}$ (SEQ ID NO:1) was subjected to substitution mutagenesis of selected codons coding for the residues situated in the loop which locates in the major groove of dsRNA (FIG. 1). Substitutions in the protein were introduced using properly designed primer pairs. The template for the PCR reaction was plasmid pET28Bsu (Example 2). The PCR reaction to amplify the variants of the coding sequences with the introduced substitutions were performed as described in Example 2 using the primer pair listed in the following Table 7.

TABLE 7

The sequences and the names of primer pairs used for the introduction of substitutions in order to obtain different endoribonuclease BSU variants in selected amino acid positions. Type of substitution is shown in Table 8.

| Position number of the amino acid residue | Primer name | Primer sequence | SEQ ID NOs: |
|---|---|---|---|
| 79 | K79Af | CCAGAGGCAGAAATGCCAAGTC | SEQ ID NO: 89 |
|  | K79Ar | CCAGCACCGCTTCCTCTTC | SEQ ID NO: 90 |

TABLE 7-continued

The sequences and the names of primer pairs used for the introduction of substitutions in order to obtain different endoribonuclease BSU variants in selected amino acid positions. Type of substitution is shown in Table 8.

| Position number of the amino acid residue | Primer name | Primer sequence | SEQ ID NOs: |
|---|---|---|---|
| 80 | R80Af | CCGGCAGAAATGCCAAGTCAGG | SEQ ID NO: 91 |
|  | R80Ar | CCTTCAGCACCGCTTCCTCTTC | SEQ ID NO: 92 |
| 82 | R82Af | CCAATGCCAAGTCAGGGACAAC | SEQ ID NO: 93 |
|  | R82Ar | CGCCTCTTTTCAGCACCGC | SEQ ID NO: 94 |
| 83 | N83Af | CTGCCAAGTCAGGGACAAC | SEQ ID NO: 95 |
|  | N83Ar | CTCTGCCTCTTTTCAGCAC | SEQ ID NO: 96 |
| 85 | K85Af | CCTCAGGGACAACACCTAAAAATACAG | SEQ ID NO: 97 |
|  | K85Ar | CCGCATTTCTGCCTCTTTTCAGC | SEQ ID NO: 98 |
| 86 | S86Af | CTGGGACAACACCTAAAAATAC | SEQ ID NO: 99 |
|  | S86Ar | CTTTGGCATTTCTGCCTC | SEQ ID NO: 100 |
| 88 | T88Af | CCACACCTAAAAATACAGATGTTC | SEQ ID NO: 101 |
|  | T88Ar | CGCCTGACTTGGCATTTC | SEQ ID NO: 102 |
| 91 | K91Af | CCAATACAGATGTTCAGACGTACCG | SEQ ID NO: 103 |
|  | K91Ar | CCGGTGTTGTCCCTGACTTG | SEQ ID NO: 104 |
| 92 | N92Af | CACAGATGTTCAGACGTACCG | SEQ ID NO: 105 |
|  | N92Ar | GCCTTAGGTGTTGTCCCTG | SEQ ID NO: 106 |
| 94 | D94Af | CCGTTCAGACGTACCGCTAC | SEQ ID NO: 107 |
|  | D94Ar | CCGTATTTTTAGGTGTTGTCCCTG | SEQ ID NO: 108 |
| 94 | D94Rf | CGTGTTCAGACGTACCGCTACAGTACAG | SEQ ID NO: 109 |
|  | D94Rr | TGTATTTTTAGGTGTTGTCCCTGACTTG | SEQ ID NO: 110 |

The procedures of phosphorylation, ligation, and constructs transformation were carried out as in Example 8. The extransformants were plated on LB agar with 50 μg/μl kanamycin. The grown colonies were inoculated as in Example 2b, the plasmids were isolated as in Example 2b. The selection of suitable transformants and confirmation of the sequence correctness of the desired substitution was based on the sequencing of the sample (SSIS DNA IBB PAS).

Example 11

Expression and Purification of Endoribonuclease BSU Protein Variants and Endonucleolytic Activity Assay 10 variants with substitutions to alanine at positions of the amino acid residues K79, R80, R82, N83, K85, S86, T88, K91, N92, D94 were prepared. Expression and purification of variants were carried out as in Example 3. Then endonucleolytic activities were examined. Results are shown in Table 8. Positions R80, R82, K85, T88, K91, N92, D94 may be involved in sequence specificity of the enzyme. They probably interact with bases in the dsRNA nucleic acid, and therefore for further substitution mutagenesis the positions were selected in which the substitution to alanine inactivated the enzyme or decreased its activity.

TABLE 8

Endoribonucleolytic activity of alanine substitution variants of endoribonuclease BSU.

| Substitution of amino acid residues in endoribonuclease BSU$^{WT}$ | Endoribonucleolytic activity of variant |
|---|---|
| K79A | + |
| R80A | +/− |
| R82A | +/−− |
| N83A | + |
| K85A | − |
| S86A | + |
| T88A | +/− |
| K91A | − |
| N92A | +/−− |
| D94A | +/−− |

Figure 5:
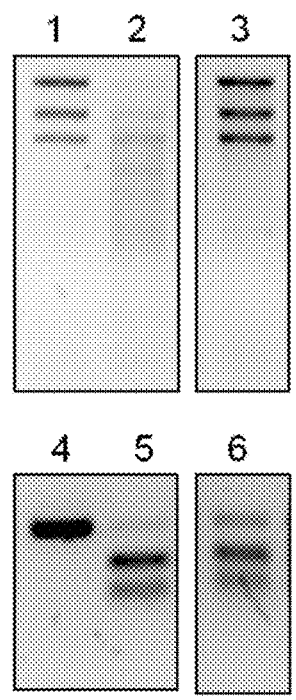
FIG. 5. Comparison of sequence preferences of endoribonuclease BSU wild-type (endoribonuclease $BSU^{WT}$) and D95R variant (endoribonuclease $BSU^{D95R}$). 1—bacteriophage Φ6 dsRNA genome, 2—bacteriophage Φ6 dsRNA genome cleaved with endoribonuclease $BSU^{WT}$, 3—bacteriophage Φ6 dsRNA genome cleaved with endoribonuclease $BSU^{D94R}$, 4—234 bp dsRNA, 5—234 bp dsRNA cleaved with endoribonuclease $BSU^{WT}$, 6—234 bp dsRNA cleaved with D94R variant.

"+"—dsRNA cleavage as for the wild type endoribonuclease BSU (BSU$^{WT}$);
"+/−"—impaired dsRNA cleavage;
"+/−−"—impaired dsRNA cleavage,
"−"—no cleavage A substitution variant to arginine at the position number 94 (D94R) was created. The protein was purified as in step 3, and its endoribonucleolytic activity was tested on two substrates: bacteriophage Φ6 genome and 234 bp dsRNA. 234 bp dsRNA, which has one preferred cleavage site, was cleaved similarly by the wild type enzyme and D94R variant. Φ6 dsRNA, which has 38 consensus cleavage sites, was not cleaved with the same efficiency by both enzymes. Cleavage by the D94R variant was impaired in comparison to the wild-type enzyme. The results obtained are shown in FIG. 5. It is shown that the variant D94R has an increased selectivity to the preferred sequence of dsRNA. Increased selectivity of the enzyme results in the narrowing of the sequence recognition and cleavage of dsRNA.

The above results indicate that the loop locating in the major groove of dsRNA determines the sequence specificity in the dsRNA cleavage determined only by the sequence of dsRNA and independent on the irregular helix structure and/or cooperation with other proteins. The method also demonstrate the selection leading to derivatives and/or variants of dsRNA endoribonucleases exhibiting increased sequence specificity in dsRNA cleavage, preferably in such a method of obtaining derivatives and/or variants with sequence specific cleavage of dsRNA the endoribonuclease derivatives and/or variants are generated with preferably altered, increased selectivity to the specific sequence in dsRNA cleavage.

Example 12

Cleavage of Three Short 30 bp dsRNAs 30 bp dsRNA substrates were prepared by annealing RNA oligonucleotides 30N1F and 30N1R, 30N2F and 30N2R, 30N3F and 30N3R described in example 4c. 30 bp dsRNA with preferred sequence prepared from oligonucleotides 30F and 30R from example 4c was used as a control. Cleavage reaction was carried out as in Example 5 using endoribonuclease BSU$^{WT}$ prepared in accordance with the Example 3. Prepared substrates were cleaved by endoribonuclease BSU$^{WT}$. Products were separated on 15% polyacrylamide gel (15% polyacrylamide, TBE: 135 mM Tris-HCl, 45 mM boric acid, 2.5 mM EDTA). Visualization of the products is described in Example 6b. The results are shown in FIG. 8. Three tested substrates are not cleaved.

The List of Sequences Identified in the Description:
SEQ ID NO:1—amino acid sequence of dsRNA endoribonuclease BSU$^{WT}$ from *Bacillus subtilis*
SEQ ID NO:2—a sequence of modified vector pKS II
SEQ ID NO:3—fragment of polypeptide chain of endoribonuclease FNU from *Fusobacterium nucleatum* forming a loop that locates in and interacts with the major groove of the dsRNA
SEQ ID NO:4—fragment of polypeptide chain of endoribonuclease BSU from *Bacillus subtilis* forming a loop that locates in and interacts with the major groove of the dsRNA
SEQ ID NO:5—fragment of polypeptide chain of endoribonuclease BCE from *Bacillus cereus* forming a loop that locates in and interacts with the major groove of the dsRNA
SEQ ID NO:6—nucleotide sequence of primer for endoribonuclease BSU gene amplification
SEQ ID NO:7—nucleotide sequence of primer for endoribonuclease BSU gene amplification
SEQ ID NO:8—nucleotide sequence of primer for endoribonuclease FNU gene amplification
SEQ ID NO:9—nucleotide sequence of primer for endoribonuclease FNU gene amplification
SEQ ID NO:10—nucleotide sequence of primer for endoribonuclease BCE gene amplification
SEQ ID NO:11—nucleotide sequence of primer for endoribonuclease BCE gene amplification
SEQ ID NO:12—nucleotide sequence of bsuRNAf primer for 234 bp dsRNA synthesis
SEQ ID NO:13—nucleotide sequence of bsuRNAr primer for 234 bp dsRNA synthesis
SEQ ID NO:14—nucleotide sequence of 18F oligonucleotide for 18 bp dsRNA preparation
SEQ ID NO:15—nucleotide sequence of 18R oligonucleotide for 18 bp dsRNA preparation
SEQ ID NO:16—nucleotide sequence of 20F oligonucleotide for 20 bp dsRNA preparation
SEQ ID NO:17—nucleotide sequence of 20R oligonucleotide for 20 bp dsRNA preparation
SEQ ID NO:18—nucleotide sequence of 22F oligonucleotide for 22 bp dsRNA preparation
SEQ ID NO:19—nucleotide sequence of 22R oligonucleotide for 22 bp dsRNA preparation
SEQ ID NO:20—nucleotide sequence of 30F oligonucleotide for 30 bp dsRNA preparation
SEQ ID NO:21—nucleotide sequence of 30R oligonucleotide for 30 bp dsRNA preparation
SEQ ID NO:22—nucleotide sequence of 30N1F oligonucleotide for N1 30 bp dsRNA preparation
SEQ ID NO:23—nucleotide sequence of 30N1R oligonucleotide for N1 30 bp dsRNA preparation
SEQ ID NO:24—nucleotide sequence of 30N2F oligonucleotide for N2 30 bp dsRNA preparation
SEQ ID NO:25—nucleotide sequence of 30N2R oligonucleotide for N2 30 bp dsRNA preparation
SEQ ID NO:26—nucleotide sequence of 30N3F oligonucleotide for N3 30 bp dsRNA preparation
SEQ ID NO:27—nucleotide sequence of 30N3R oligonucleotide for N3 30 bp dsRNA preparation
SEQ ID NO:28—nucleotide sequence of RTr primer for reverse transcription reaction
SEQ ID NO:29—nucleotide sequence of RTf primer for reverse transcription reaction
SEQ ID NO:30—nucleotide sequence of 234 bp dsRNA substrate
SEQ ID NO:31—nucleotide sequence of Subf primer for substitution library creation of 234 bp dsRNA
SEQ ID NO:32—nucleotide sequence of Sub83r primer for substitution library creation of 234 bp dsRNA
SEQ ID NO:33—nucleotide sequence of Sub84r primer for substitution library creation of 234 bp dsRNA
SEQ ID NO:34—nucleotide sequence of Sub85r primer for substitution library creation of 234 bp dsRNA
SEQ ID NO:35—nucleotide sequence of Sub86r primer for substitution library creation of 234 bp dsRNA
SEQ ID NO:36—nucleotide sequence of Sub87r primer for substitution library creation of 234 bp dsRNA
SEQ ID NO:37—nucleotide sequence of Sub88r primer for substitution library creation of 234 bp dsRNA
SEQ ID NO:38—nucleotide sequence of Sub89r primer for substitution library creation of 234 bp dsRNA
SEQ ID NO:39—nucleotide sequence of Subr primer for substitution library creation of 234 bp dsRNA
SEQ ID NO:40—nucleotide sequence of Sub90f primer for substitution library creation of 234 bp dsRNA
SEQ ID NO:41—nucleotide sequence of Sub91f primer for substitution library creation of 234 bp dsRNA
SEQ ID NO:42—nucleotide sequence of Sub92f primer for substitution library creation of 234 bp dsRNA
SEQ ID NO:43—nucleotide sequence of Sub93f primer for substitution library creation of 234 bp dsRNA
SEQ ID NO:44—nucleotide sequence of Sub94f primer for substitution library creation of 234 bp dsRNA
SEQ ID NO:45—nucleotide sequence of Sub95f primer for substitution library creation of 234 bp dsRNA
SEQ ID NO:46—nucleotide sequence of Sub96f primer for substitution library creation of 234 bp dsRNA
SEQ ID NO:47—nucleotide sequence of 83G 234 bp dsRNA SEQ ID NO:48—nucleotide sequence of 83A 234 bp dsRNA
SEQ ID NO:49—nucleotide sequence of 83U 234 bp dsRNA
SEQ ID NO:50—nucleotide sequence of 84A 234 bp dsRNA
SEQ ID NO:51—nucleotide sequence of 84U 234 bp dsRNA
SEQ ID NO:52—nucleotide sequence of 84C 234 bp dsRNA
SEQ ID NO:53—nucleotide sequence of 85G 234 bp dsRNA
SEQ ID NO:54—nucleotide sequence of 85A 234 bp dsRNA
SEQ ID NO:55—nucleotide sequence of 85C 234 bp dsRNA
SEQ ID NO:56—nucleotide sequence of 86G 234 bp dsRNA
SEQ ID NO:57—nucleotide sequence of 86A 234 bp dsRNA
SEQ ID NO:58—nucleotide sequence of 86U 234 bp dsRNA
SEQ ID NO:59—nucleotide sequence of 87A 234 bp dsRNA
SEQ ID NO:60—nucleotide sequence of 87U 234 bp dsRNA
SEQ ID NO:61—nucleotide sequence of 87C 234 bp dsRNA
SEQ ID NO:62—nucleotide sequence of 88G 234 bp dsRNA
SEQ ID NO:63—nucleotide sequence of 88U 234 bp dsRNA
SEQ ID NO:64—nucleotide sequence of 88C 234 bp dsRNA
SEQ ID NO:65—nucleotide sequence of 89G 234 bp dsRNA
SEQ ID NO:66—nucleotide sequence of 89A 234 bp dsRNA
SEQ ID NO:67—nucleotide sequence of 89U 234 bp dsRNA
SEQ ID NO:68—nucleotide sequence of 90G 234 bp dsRNA
SEQ ID NO:69—nucleotide sequence of 90A 234 bp dsRNA
SEQ ID NO:70—nucleotide sequence of 90U 234 bp dsRNA
SEQ ID NO:71—nucleotide sequence of 91G 234 bp dsRNA
SEQ ID NO:72—nucleotide sequence of 91A 234 bp dsRNA
SEQ ID NO:73—nucleotide sequence of 91C 234 bp dsRNA
SEQ ID NO:74—nucleotide sequence of 92G 234 bp dsRNA
SEQ ID NO:75—nucleotide sequence of 92A 234 bp dsRNA
SEQ ID NO:76—nucleotide sequence of 92U 234 bp dsRNA
SEQ ID NO:77—nucleotide sequence of 93A 234 bp dsRNA
SEQ ID NO:78—nucleotide sequence of 93U 234 bp dsRNA
SEQ ID NO:79—nucleotide sequence of 93C 234 bp dsRNA
SEQ ID NO:80—nucleotide sequence of 94G 234 bp dsRNA
SEQ ID NO:81—nucleotide sequence of 94U 234 bp dsRNA
SEQ ID NO:82—nucleotide sequence of 94C 234 bp dsRNA
SEQ ID NO:83—nucleotide sequence of 95A 234 bp dsRNA
SEQ ID NO:84—nucleotide sequence of 95U 234 bp dsRNA
SEQ ID NO:85—nucleotide sequence of 95C 234 bp dsRNA
SEQ ID NO:86—nucleotide sequence of 96A 234 bp dsRNA
SEQ ID NO:87—nucleotide sequence of 96U 234 bp dsRNA
SEQ ID NO:88—nucleotide sequence of 96C 234 bp dsRNA
SEQ ID NO:89—nucleotide sequence of K79Af primer
SEQ ID NO:90—nucleotide sequence of K79Ar primer
SEQ ID NO:91—nucleotide sequence of R80Af primer
SEQ ID NO:92—nucleotide sequence of R82Ar primer
SEQ ID NO:93—nucleotide sequence of R82Af primer
SEQ ID NO:94—nucleotide sequence of R82Ar primer
SEQ ID NO:95—nucleotide sequence of N83Af primer
SEQ ID NO:96—nucleotide sequence of N83Ar primer
SEQ ID NO:97—nucleotide sequence of K85Af primer
SEQ ID NO:98—nucleotide sequence of K85Ar primer
SEQ ID NO:99—nucleotide sequence of S86Af primer
SEQ ID NO:100—nucleotide sequence of S86Ar primer
SEQ ID NO:101—nucleotide sequence of T88Af primer
SEQ ID NO:102—nucleotide sequence of T88Ar primer
SEQ ID NO:103—nucleotide sequence of K91Af primer
SEQ ID NO:104—nucleotide sequence of K91Ar primer
SEQ ID NO:105—nucleotide sequence of N92Af primer
SEQ ID NO:106—nucleotide sequence of N92Ar primer
SEQ ID NO:107—nucleotide sequence of D94Af primer
SEQ ID NO:108—nucleotide sequence of D94Ar primer
SEQ ID NO:109—nucleotide sequence of D94Rf primer
SEQ ID NO:110—nucleotide sequence of D94Rr primer The invention is further described by the following numbered paragraphs:

1. Use dsRNA endoribonuclease for sequence specific cleavage of dsRNA substrate, wherein said endoribonuclease comprises amino acid sequence of SEQ ID NO:1 or SEQ ID NO:1 with D94R mutation; and has the loop that is locating in and interacting with a major groove of dsRNA, which corresponds to the loop locating in and interacting with a major groove of dsRNA in the model of structure of endoribonuclease Mini III in complex with dsRNA; and wherein said dsRNA endoribonuclease exhibits the dsRNA sequence specific activity within the consensus sequence (SEQ ID NOS: 111 and 121)

```
5' DACCUHD 3'

3' HUGGADH 5'
``` where H=A or C or U; D=A or G or U; preferably said dsRNA endoribonuclease exhibits the dsRNA sequence specific activity within the consensus sequence (SEQ ID NOS: 112 and 122)

```
5' YGACCUCCNNG 3'

3' RCUGGAGCNNC 5'
``` where Y=C or U; R=A or G; N=G or A or U or C, and wherein the specific sequence in dsRNA substrate recognized by said dsRNA endoribonuclease is the consensus sequence (SEQ ID NOS: 111 and 121)

```
5' DACCUHD 3'
3' HUGGADH 5'
``` where H=A or C or U; D=A or G or U; preferably is the consensus sequence (SEQ ID NOS: 112 and 122)

```
5' YGACCUCGNNG 3'
3' RCUGGAGCNNC 5'
``` where Y=C or U; R=A or G; N=G or A or U or C, and wherein said dsRNA substrate comprises and is cleaved within said recognition sequence by said dsRNA endoribonuclease.

2. A method of sequence specific cleavage of dsRNA substrate by dsRNA endoribonuclease, comprising the steps
   a) combining the dsRNA endoribonuclease with dsRNA substrate in a mixture,
   wherein said dsRNA endoribonuclease and comprises amino acid sequence of SEQ ID NO:1 or SEQ ID NO:1 with D94R mutation; and has the loop that is locating in and interacting with a major groove of dsRNA, which corresponds to the loop locating in and interacting with a major groove of dsRNA in the model of structure of endoribonuclease Mini III in complex with dsRNA; and wherein said dsRNA endoribonuclease exhibits the dsRNA sequence specific activity within the consensus sequence (SEQ ID NOS: 111 and 121)

```
5' DACCUHD 3'
3' HUGGADH 5'
``` where H=A or C or U; D=A or G or U; preferably said dsRNA endoribonuclease exhibits the dsRNA sequence specific activity within the consensus sequence (SEQ ID NOS: 112 and 122)

```
5' YGACCUCGNNG 3'
3' RCUGGAGCNNC 5'
``` where Y=C or U; R=A or G; N=G or A or U or C; and wherein the specific sequence in dsRNA substrate recognized by said dsRNA endoribonuclease is the consensus sequence (SEQ ID NOS: 111 and 121)

```
5' DACCUHD 3'
3' HUGGADH 5'
``` where H=A or C or U; D=A or G or U; preferably is the consensus sequence (SEQ ID NOS: 112 and 122)

```
5' YGACCUCGNNG 3'
3' RCUGGAGCNNC 5'
``` where Y=C or U; R=A or G; N=G or A or U or C, b) cleaving the said dsRNA substrate within said recognition sequence by said dsRNA endoribonuclease.

3. The method of sequence specific cleavage of dsRNA substrate according to paragraph 2, wherein the cleaving of dsRNA is performed in temperature from 35° C. till 45° C.; and/or in sodium chloride concentration from 5 to 60 mM; and preferably in $Mg^{2+}$ concentration of 1 to 2.5 mM.

4. An dsRNA endoribonuclease, wherein dsRNA endoribonuclease comprises amino acid sequence of SEQ ID NO:1 with D94R mutation; and has the loop that is locating in and interacting with a major groove of dsRNA, which corresponds to the loop locating in and interacting with a major groove of dsRNA in the model of structure of endoribonuclease Mini III in complex with dsRNA; and wherein the specific sequence in dsRNA substrate recognized by said dsRNA endoribonuclease is the consensus sequence (SEQ ID NOS: 111 and 121)

```
5' DACCUHD 3'
3' HUGGADH 5'
``` where H=A or C or U; D=A or G or U; preferably is the consensus sequence (SEQ ID NOS: 112 and 122)

```
5' YGACCUCGNNG 3'
3' RCUGGAGCNNC 5'
``` where Y=C or U; R=A or G; N=G or A or U or C; and wherein said dsRNA endoribonuclease exhibits the dsRNA sequence specific activity within said consensus sequence.

5. A method for producing dsRNA endoribonuclease, wherein the method comprises the step of expressing of dsRNA endoribonuclease as defined in paragraph 4.

6. A genetic construct, characterized in that it comprises the nucleotide sequence encoding the dsRNA endoribonuclease as defined in paragraph 4.

7. A host cell comprising the genetic construct as defined in paragraph 6.

8. The kit, wherein it comprises the dsRNA endoribonuclease as defined in paragraph 4.

9. Use of the dsRNA endoribonuclease for sequence specific cleavage of dsRNA substrate, wherein said endoribonuclease comprises dsRNA endoribonuclease FNU from *Fusobacterium nucleatum* or dsRNA endoribonuclease BCE from *Bacillus cereus*, and has the loop that is locating in and interacting with a major groove of dsRNA, which corresponds to the loop locating in and interacting with a major groove of dsRNA in the model of structure of endoribonuclease Mini III in complex with dsRNA; and wherein the dsRNA substrate does not have the irregular helix structure in one or both strands of dsRNA within the specific sequence recognized bp dsRNA endoribonuclease, and wherein said dsRNA substrate is cleaved by said dsRNA endoribonuclease within the specific sequence recognized by said dsRNA endoribonuclease depending only on the sequence of dsRNA and not on the existence of irregular helix structure in one or both strands of dsRNA within the specific sequence recognized by said dsRNA endoribonuclease and/or interaction of other assisting proteins; and wherein said dsRNA substrate comprises and is cleaved within said recognition sequence by said dsRNA endoribonuclease.

10. A method of sequence specific cleavage of dsRNA substrate by dsRNA endoribonuclease, comprising the steps
   a) combining the dsRNA endoribonuclease with dsRNA substrate in a mixture, wherein said endoribonuclease comprises dsRNA endoribonuclease FNU from *Fusobacterium nucleatum* or dsRNA endoribonuclease BCE from *Bacillus cereus*, and has the loop that is locating in and interacting with a major groove of dsRNA, which corresponds to the loop locating in and interacting with a major groove of dsRNA in the model of structure of endoribonuclease Mini III in complex with dsRNA; and wherein the dsRNA substrate does not have the irregular helix structure in one or both strands of dsRNA within the specific sequence recognized bp dsRNA endoribonuclease, and wherein said dsRNA substrate is cleaved by said dsRNA endoribonuclease within the specific sequence recognized by said dsRNA endoribonuclease depending only on the sequence of dsRNA and not on the existence of irregular helix structure in one or both strands of dsRNA within the specific sequence recognized by said dsRNA endoribonuclease and/or interaction of other assisting proteins;

b) cleaving the said dsRNA substrate within said recognition sequence by said dsRNA endoribonuclease.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A method of sequence specific cleavage of dsRNA substrate by a dsRNA endoribonuclease, comprising the steps of
a) combining the dsRNA endoribonuclease with dsRNA substrate in a mixture, wherein said dsRNA endoribonuclease comprises amino acid sequence of SEQ ID NO:1 with a D94R mutation; and has the loop that is locating in and interacting with a major groove of dsRNA, which corresponds to the loop locating in and interacting with a major groove of dsRNA in the model of structure of endoribonuclease Mini III in complex with dsRNA; and wherein said dsRNA endoribonuclease exhibits the dsRNA sequence specific activity within the consensus sequence (SEQ ID NOS: 111 and 121)
5' DACCUHD 3'
3' HUGGADH 5'
where H=A or C or U; D=A or G or U; preferably said dsRNA endoribonuclease exhibits the dsRNA sequence specific activity within the consensus sequence SEQ ID NOS: 112 and 122)
5' YGACCUCGNNG 3'
3' RCUGGAGCNNC 5'
where Y=C or U; R=A or G; N=G or A or U or C; and wherein the specific sequence in dsRNA substrate recognized by said dsRNA endoribonuclease is the consensus sequence (SEQ ID NOS: 111 and 121)
5' DACCUHD 3'
3' HUGGADH 5'
where H=A or C or U; D=A or G or U; preferably is the consensus sequence (SEQ ID NOS: 112 and 122)
5' YGACCUCGNNG 3'
3' RCUGGAGCNNC 5'
where Y=C or U; R=A or G; N=G or A or U or C,
b) cleaving the said dsRNA substrate within said recognition sequence by said dsRNA endoribonuclease.

2. The method of sequence specific cleavage of dsRNA substrate according to claim 1, wherein the cleaving of ds RNA is performed in temperature from 35° C. till 45° C.; and/or in sodium chloride concentration from 5 to 60 mM; and preferably in $Mg^{2+}$ concentration of 1 to 2.5 mM.

3. An dsRNA endoribonuclease, wherein dsRNA endoribonuclease comprises amino acid sequence of SEQ ID NO:1 with D94R mutation; and has the loop that is locating in and interacting with a major groove of dsRNA, which corresponds to the loop locating in and interacting with a major groove of dsRNA in the model of structure of endoribonuclease Mini III in complex with dsRNA; and wherein the specific sequence in dsRNA substrate recognized by said dsRNA endoribonuclease is the consensus sequence (SEQ ID NOS: 111 and 121)
5' DACCUHD 3'
3' HUGGADH 5'
where H=A or C or U; D=A or G or U; preferably is the consensus sequence (SEQ ID NOS: 112 and 122)
5' YGACCUCGNNG 3'
3' RCUGGAGCNNC 5'
where Y=C or U; R=A or G; N=G or A or U or C; and wherein said dsRNA endoribonuclease exhibits the dsRNA sequence specific activity within said consensus sequence.

4. A method for producing dsRNA endoribonuclease, wherein the method comprises the step of expressing of dsRNA endoribonuclease as defined in claim 3.

5. A genetic construct, characterized in that it comprises the nucleotide sequence encoding the dsRNA endoribonuclease as defined in claim 3.

6. A host cell comprising the genetic construct as defined in claim 5.

7. The kit, wherein it comprises the dsRNA endoribonuclease as defined in claim 3.

8. A method for sequence specific cleavage of a dsRNA substrate with a dsRNA endoribonuclease comprising an amino acid sequence of SEQ ID NO:1 with a D94R mutation; and has the loop that is locating in and interacting with a major groove of dsRNA, which corresponds to the loop locating in and interacting with a major groove of dsRNA in the model of structure of endoribonuclease Mini III in complex with dsRNA; and wherein said dsRNA endoribonuclease exhibits the dsRNA sequence specific activity within the consensus sequence (SEQ ID NOS: 111 and 121)
5' DACCUHD 3'
3' HUGGADH 5'
where H=A or C or U; D=A or G or U; preferably said dsRNA endoribonuclease exhibits the dsRNA sequence specific activity within the consensus sequence (SEQ ID NOS: 112 and 122)
5' YGACCUCGNNG 3'
3' RCUGGAGCNNC 5' where Y=C or U; R=A or G; N=G or A or U or C, and wherein the specific sequence in dsRNA substrate recognized by said dsRNA endoribonuclease is the consensus sequence (SEQ ID NOS: 111 and 121)

5' DACCUHD 3'
   3' HUGGADH 5' where H=A or C or U; D=A or G or U; preferably is the consensus sequence (SEQ ID NOS: 112 and 122)

5' YGACCUCGNNG 3'
   3' RCUGGAGCNNC 5' where Y=C or U; R=A or G; N=G or A or U or C, and wherein said dsRNA substrate comprises and is cleaved within said recognition sequence by said dsRNA endoribonuclease.

\* \* \* \* \*

SEQUENCE LISTING

<160> NUMBER OF SEQ ID NOS: 122

<210> SEQ ID NO 1
<211> LENGTH: 142
<212> TYPE: PRT
<213> ORGANISM: Bacillus subtilis

<400> SEQUENCE: 1

```
Leu Glu Phe Asp Thr Ile Lys Asp Ser Lys Gln Leu Asn Gly Leu Ala
1               5                   10                  15

Leu Ala Tyr Ile Gly Asp Ala Ile Phe Glu Val Tyr Val Arg His His
            20                  25                  30

Leu Leu Lys Gln Gly Phe Thr Lys Pro Asn Asp Leu His Lys Lys Ser
        35                  40                  45

Ser Arg Ile Val Ser Ala Lys Ser Gln Ala Glu Ile Leu Phe Phe Leu
    50                  55                  60

Gln Asn Gln Ser Phe Phe Thr Glu Glu Glu Ala Val Leu Lys Arg
65                  70                  75                  80

Gly Arg Asn Ala Lys Ser Gly Thr Thr Pro Lys Asn Thr Asp Val Gln
                85                  90                  95

Thr Tyr Arg Tyr Ser Thr Ala Phe Glu Ala Leu Leu Gly Tyr Leu Phe
                100                 105                 110

Leu Glu Lys Lys Glu Glu Arg Leu Ser Gln Leu Val Ala Glu Ala Ile
            115                 120                 125

Gln Phe Gly Thr Ser Gly Arg Lys Thr Asn Glu Ser Ala Thr
        130                 135                 140
```

<210> SEQ ID NO 2
<211> LENGTH: 2949
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ctaaattgta agcgttaata ttttgttaaa attcgcgtta aatttttgtt aaatcagctc      60 atttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
```

```
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggatccc ccacaatcct    660
gtcgttacct gtcatgtatc cgtctagatg ggctgcagga attcgatatc aagcttatcg    720
ataccgtcga ccgggggggc ccggtaccca gcttttgttc cctttagtga ggttaattg     780
cgcgcttggc gtaatcatgg tcatagctgt ttcctgtgtg aaattgttat ccgctcacaa    840
ttccacacaa catacgagcc ggaagcataa agtgtaaagc ctggggtgcc taatgagtga    900
gctaactcac attaattgcg ttgcgctcac tgcccgcttt ccagtcggga aacctgtcgt    960
gccagctgca ttaatgaatc ggccaacgcg cggggagagg cggtttgcgt attgggcgct   1020
cttccgcttc ctcgctcact gactcgctgc gctcggtcgt tcggctgcgg cgagcggtat   1080
cagctcactc aaaggcggta atacggttat ccacagaatc aggggataac gcaggaaaga   1140
acatgtgagc aaaaggccag caaaaggcca ggaaccgtaa aaaggccgcg ttgctggcgt   1200
ttttccatag gctccgcccc cctgacgagc atcacaaaaa tcgacgctca agtcagaggt   1260
ggcgaaaccc gacaggacta taaagatacc aggcgtttcc ccctggaagc tccctcgtgc   1320
gctctcctgt tccgaccctg ccgcttaccg gatacctgtc cgcctttctc ccttcgggaa   1380
gcgtggcgct ttctcatagc tcacgctgta ggtatctcag ttcggtgtag tcgttcgct    1440
ccaagctggg ctgtgtgcac gaaccccccg ttcagcccga ccgctgcgcc ttatccggta   1500
actatcgtct tgagtccaac ccggtaagac acgacttatc gccactggca gcagccactg   1560
gtaacaggat tagcagagcg aggtatgtag gcggtgctac agagttcttg aagtggtggc   1620
ctaactacgg ctacactaga aggacagtat ttggtatctg cgctctgctg aagccagtta   1680
ccttcggaaa aagagttggt agctcttgat ccggcaaaca aaccaccgct ggtagcggtg   1740
gtttttttgt ttgcaagcag cagattacgc gcagaaaaaa aggatctcaa gaagatcctt   1800
tgatcttttc tacggggtct gacgctcagt ggaacgaaaa ctcacgttaa gggattttgg   1860
tcatgagatt atcaaaaagg atcttcacct agatcctttt aaattaaaaa tgaagtttta   1920
aatcaatcta agtatatat gagtaaactt ggtctgacag ttaccaatgc ttaatcagtg   1980
aggcacctat ctcagcgatc tgtctatttc gttcatccat agttgcctga ctccccgtcg   2040
tgtagataac tacgatacgg gagggcttac catctggccc cagtgctgca atgataccgc   2100
gagacccacg ctcaccggct ccagatttat cagcaataaa ccagccagcc ggaagggccg   2160
agcgcagaag tggtcctgca actttatccg cctccatcca gtctattaat gttgccggg    2220
aagctagagt aagtagttcg ccagttaata gtttgcgcaa cgttgttgcc attgctacag   2280
gcatcgtggt gtcacgctcg tcgtttggta tggcttcatt cagctccggt tcccaacgat   2340
caaggcgagt tacatgatcc cccatgttgt gcaaaaaagc ggttagctcc ttcggtcctc   2400
cgatcgttgt cagaagtaag ttggccgcag tgttatcact catggttatg gcagcactgc   2460
ataattctct tactgtcatg ccatccgtaa gatgcttttc tgtgactggt gagtactcaa   2520
ccaagtcatt ctgagaatag tgtatgcggc gaccgagttg ctcttgcccg gcgtcaatac   2580
gggataatac cgcgccacat agcagaactt taaaagtgct catcattgga aaacgttctt   2640
cggggcgaaa actctcaagg atcttaccgc tgttgagatc cagttcgatg taacccactc   2700
gtgcacccaa ctgatcttca gcatctttta ctttcaccag cgtttctggg tgagcaaaaa   2760
caggaaggca aaatgccgca aaaaagggaa taagggcgac acggaaatgt tgaatactca   2820
```

```
tactcttcct ttttcaatat tattgaagca tttatcaggg ttattgtctc atgagcggat    2880
acatatttga atgtatttag aaaaataaac aataggggt tccgcgcaca tttccccgaa     2940
aagtgccac                                                            2949
```

<210> SEQ ID NO 3
<211> LENGTH: 14
<212> TYPE: PRT
<213> ORGANISM: Fusobacterium nucleatum

<400> SEQUENCE: 3

```
Ala Lys Asn Ser Asn Ile Lys Thr Phe Pro Arg Ser Cys Thr
1               5                   10
```

<210> SEQ ID NO 4
<211> LENGTH: 14
<212> TYPE: PRT
<213> ORGANISM: Bacillus subtilis

<400> SEQUENCE: 4

```
Gly Arg Asn Ala Lys Ser Gly Thr Thr Pro Lys Asn Thr Asp
1               5                   10
```

<210> SEQ ID NO 5
<211> LENGTH: 14
<212> TYPE: PRT
<213> ORGANISM: Bacillus cereus

<400> SEQUENCE: 5

```
Gly Arg Asn Ala Asn Ser Gly Thr Val Pro Lys Asn Thr Asp
1               5                   10
```

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tacccatatg cttgaatttg atacg                                          25
```

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tactcgagtc atgttgctga ctcatttg                                       28
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ccgcatatgg acaatgtaga tttttcaaag                                     30
```

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgctcgagt catcattctc cctttataac tatatttata atttttttta tttc          54

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgcatatgg tcgatgcaaa gcaattaaac ag                                  32

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tactcgagtc atgatgatgt gccccttc                                       29

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgcgtaata cgactcacta taggg                                          25

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaaaaaaat ccggctcgta tgttgtg                                        27

<210> SEQ ID NO 14
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
accgucgacc ucgagggg                                                  18

```
<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ccccucgagg ucgacggu                                                    18

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
auaccgucga ccucgagggg                                                  20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ccccucgagg ucgacgguau                                                  20

<210> SEQ ID NO 18
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
auaccgucga ccucgagggg gg                                               22

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cccccccuga ggucgacggu au                                               22

<210> SEQ ID NO 20
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cgauaccguc gaccucgagg gggggcccgg                                       30

<210> SEQ ID NO 21
```

```
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ccgggccccc ccucgugguc gacgguaucg                                        30

<210> SEQ ID NO 22
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucgaguugcc gguugcugug auggccguuc                                        30

<210> SEQ ID NO 23
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gaacggccau cacagcaacc ggcaacucga                                        30

<210> SEQ ID NO 24
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ccacucuuag auacccgauu ccccuguuuc                                        30

<210> SEQ ID NO 25
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gaaacagggg aaucggguau cuaagagugg                                        30

<210> SEQ ID NO 26
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ucugaugggc gcuaccgguu ccgguaaguc                                        30

<210> SEQ ID NO 27
<211> LENGTH: 30
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gacuuaccgg aaccgguagc gcccaucaga                                      30

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaaacagcta tgaccatga                                                  19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gatcccccac aatcctgtc                                                  19

<210> SEQ ID NO 30
<211> LENGTH: 234
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 30 gggaucccc  acaauccugu  cguuaccugu  cauguauccg  ucuagauggg  cugcaggaau     60
ucgauaucaa  gcuuaucgau  accgucgacc  ucgagggggg  gcccgguacc  cagcuuuugu    120
ucccuuuagu  gagggguuaau  ugcgcgcuug  gcguaaucau  ggucauagcu  guuuccugug   180
ugaaauuguu  auccgcucac  aauuccacac  aacauacgag  ccggauuuuu  uucc          234

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcgaggggg ggcccggta                                                  19

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 32
gtcgachgta tcgataagct tg                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtcgadggta tcgataagct tg                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtcgbcggta tcgataagct tg                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtchacggta tcgataagct tg                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtdgacggta tcgataagct tg                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gvcgacggta tcgataagct tg                                              22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 38
htcgacggta tcgataagct tg                                    22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtcgacggta tcgataagct tg                                    22

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
dtcgaggggg ggcccggta                                        19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cvcgaggggg ggcccggta                                        19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42 ctdgagggggg ggcccggta                                       19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctchaggggg ggcccggta                                        19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctcgbggggg ggcccggta                                                19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctcgahgggg ggcccggta                                                19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctcgaghggg ggcccggta                                                19

<210> SEQ ID NO 47
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 47 gggaucccccc acaauccugu cguuaccugu cauguauccg ucuagauggg cugcaggaau    60
ucgauaucaa gcuuaucgau acggucgacc ucgaggggg gcccgguacc cagcuuuugu    120
ucccuuuagu gagguuaauu ugcgcgcuug gcguaaucau ggucauagcu guuuccugug    180
ugaaauuguu auccgcucac aauuccacac aacauacgag ccggauuuuu uucc          234

<210> SEQ ID NO 48
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 48 gggaucccccc acaauccugu cguuaccugu cauguauccg ucuagauggg cugcaggaau    60
ucgauaucaa gcuuaucgau acagucgacc ucgaggggg gcccgguacc cagcuuuugu    120
ucccuuuagu gagguuaauu ugcgcgcuug gcguaaucau ggucauagcu guuuccugug    180
ugaaauuguu auccgcucac aauuccacac aacauacgag ccggauuuuu uucc          234

<210> SEQ ID NO 49
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 49 gggaucccccc acaauccugu cguuaccugu cauguauccg ucuagauggg cugcaggaau    60

```
ucgauaucaa gcuuaucgau acugucgacc ucgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234
```

<210> SEQ ID NO 50
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 50

```
gggaucccccc acaauccugu cguuaccugu cauguauccg ucuagauggg cugcaggaau    60
ucgauaucaa gcuuaucgau accaucgacc ucgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234
```

<210> SEQ ID NO 51
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 51

```
gggaucccccc acaauccugu cguuaccugu cauguauccg ucuagauggg cugcaggaau    60
ucgauaucaa gcuuaucgau accuucgacc ucgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234
```

<210> SEQ ID NO 52
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 52

```
gggaucccccc acaauccugu cguuaccugu cauguauccg ucuagauggg cugcaggaau    60
ucgauaucaa gcuuaucgau acccucgacc ucgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234
```

<210> SEQ ID NO 53
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 53

```
gggaucccccc acaauccugu cguuaccugu cauguauccg ucuagauggg cugcaggaau    60
ucgauaucaa gcuuaucgau accggcgacc ucgagggggg gcccgguacc cagcuuuugu    120
```

```
ucccuuuagu gaggguuaau ugcgcgcuug gcguaaucau ggucauagcu guuuccugug      180
ugaaauuguu auccgcucac aauuccacac aacauacgag ccggauuuuu uucc            234
```

<210> SEQ ID NO 54
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 54

```
gggauccccc acaauccugu cguuaccugu cauguauccg ucuagauggg cugcaggaau      60
ucgauaucaa gcuuaucgau accgacgacc ucgagggggg gcccgguacc cagcuuuugu     120
ucccuuuagu gaggguuaau ugcgcgcuug gcguaaucau ggucauagcu guuuccugug     180
ugaaauuguu auccgcucac aauuccacac aacauacgag ccggauuuuu uucc           234
```

<210> SEQ ID NO 55
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 55

```
gggauccccc acaauccugu cguuaccugu cauguauccg ucuagauggg cugcaggaau      60
ucgauaucaa gcuuaucgau accgccgacc ucgagggggg gcccgguacc cagcuuuugu     120
ucccuuuagu gaggguuaau ugcgcgcuug gcguaaucau ggucauagcu guuuccugug     180
ugaaauuguu auccgcucac aauuccacac aacauacgag ccggauuuuu uucc           234
```

<210> SEQ ID NO 56
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 56

```
gggauccccc acaauccugu cguuaccugu cauguauccg ucuagauggg cugcaggaau      60
ucgauaucaa gcuuaucgau accguggacc ucgagggggg gcccgguacc cagcuuuugu     120
ucccuuuagu gaggguuaau ugcgcgcuug gcguaaucau ggucauagcu guuuccugug     180
ugaaauuguu auccgcucac aauuccacac aacauacgag ccggauuuuu uucc           234
```

<210> SEQ ID NO 57
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 57

```
gggauccccc acaauccugu cguuaccugu cauguauccg ucuagauggg cugcaggaau      60
ucgauaucaa gcuuaucgau accguagacc ucgagggggg gcccgguacc cagcuuuugu     120
ucccuuuagu gaggguuaau ugcgcgcuug gcguaaucau ggucauagcu guuuccugug     180
ugaaauuguu auccgcucac aauuccacac aacauacgag ccggauuuuu uucc           234
```

<210> SEQ ID NO 58
<211> LENGTH: 234
<212> TYPE: RNA
<213> ORGANISM: Artificial Sequence
<220> FEATURE:
<223> OTHER INFORMATION: Description of Artificial Sequence: Synthetic
    dsRNA substrate sequence

<400> SEQUENCE: 58 gggaucccccc acaauccugu cguuaccugu cauguauccg ucuagauggg cugcaggaau    60
ucgauaucaa gcuuaucgau accguugacc ucgagggggg gcccgguacc cagcuuuugu   120
ucccuuuagu gaggguuaau ugcgcgcuug gcguaaucau ggucauagcu guuuccugug   180
ugaaauuguu auccgcucac aauuccacac aacauacgag ccggauuuuu uucc         234

<210> SEQ ID NO 59
<211> LENGTH: 234
<212> TYPE: RNA
<213> ORGANISM: Artificial Sequence
<220> FEATURE:
<223> OTHER INFORMATION: Description of Artificial Sequence: Synthetic
    dsRNA substrate sequence

<400> SEQUENCE: 59 gggaucccccc acaauccugu cguuaccugu cauguauccg ucuagauggg cugcaggaau    60
ucgauaucaa gcuuaucgau accgucaacc ucgagggggg gcccgguacc cagcuuuugu   120
ucccuuuagu gaggguuaau ugcgcgcuug gcguaaucau ggucauagcu guuuccugug   180
ugaaauuguu auccgcucac aauuccacac aacauacgag ccggauuuuu uucc         234

<210> SEQ ID NO 60
<211> LENGTH: 234
<212> TYPE: RNA
<213> ORGANISM: Artificial Sequence
<220> FEATURE:
<223> OTHER INFORMATION: Description of Artificial Sequence: Synthetic
    dsRNA substrate sequence

<400> SEQUENCE: 60 gggaucccccc acaauccugu cguuaccugu cauguauccg ucuagauggg cugcaggaau    60
ucgauaucaa gcuuaucgau accgucuacc ucgagggggg gcccgguacc cagcuuuugu   120
ucccuuuagu gaggguuaau ugcgcgcuug gcguaaucau ggucauagcu guuuccugug   180
ugaaauuguu auccgcucac aauuccacac aacauacgag ccggauuuuu uucc         234

<210> SEQ ID NO 61
<211> LENGTH: 234
<212> TYPE: RNA
<213> ORGANISM: Artificial Sequence
<220> FEATURE:
<223> OTHER INFORMATION: Description of Artificial Sequence: Synthetic
    dsRNA substrate sequence

<400> SEQUENCE: 61 gggaucccccc acaauccugu cguuaccugu cauguauccg ucuagauggg cugcaggaau    60
ucgauaucaa gcuuaucgau accguccacc ucgagggggg gcccgguacc cagcuuuugu   120
ucccuuuagu gaggguuaau ugcgcgcuug gcguaaucau ggucauagcu guuuccugug   180
ugaaauuguu auccgcucac aauuccacac aacauacgag ccggauuuuu uucc         234

<210> SEQ ID NO 62
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 62 gggaucccccc acaauccugu cguuaccugu cauguauccg ucuagauggg cugcaggaau    60
ucgauaucaa gcuuaucgau accgucggcc ucgagggggg gcccgguacc cagcuuuugu    120
ucccuuuagu gaggguuaau ugcgcgcuug gcguaaucau ggucauagcu guuccugug    180 ugaaauuguu auccgcucac aauuccacac aacauacgag ccggauuuuu uucc          234

<210> SEQ ID NO 63
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 63 gggaucccccc acaauccugu cguuaccugu cauguauccg ucuagauggg cugcaggaau    60
ucgauaucaa gcuuaucgau accgucgucc ucgagggggg gcccgguacc cagcuuuugu    120
ucccuuuagu gaggguuaau ugcgcgcuug gcguaaucau ggucauagcu guuccugug    180 ugaaauuguu auccgcucac aauuccacac aacauacgag ccggauuuuu uucc          234

<210> SEQ ID NO 64
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 64 gggaucccccc acaauccugu cguuaccugu cauguauccg ucuagauggg cugcaggaau    60
ucgauaucaa gcuuaucgau accgucgccc ucgagggggg gcccgguacc cagcuuuugu    120
ucccuuuagu gaggguuaau ugcgcgcuug gcguaaucau ggucauagcu guuccugug    180 ugaaauuguu auccgcucac aauuccacac aacauacgag ccggauuuuu uucc          234

<210> SEQ ID NO 65
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 65 gggaucccccc acaauccugu cguuaccugu cauguauccg ucuagauggg cugcaggaau    60
ucgauaucaa gcuuaucgau accgucgagc ucgagggggg gcccgguacc cagcuuuugu    120
ucccuuuagu gaggguuaau ugcgcgcuug gcguaaucau ggucauagcu guuccugug    180 ugaaauuguu auccgcucac aauuccacac aacauacgag ccggauuuuu uucc          234

<210> SEQ ID NO 66

<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 66
gggauccccc acaauccugu cguuaccugu cauguauccg ucuagauggg cugcaggaau    60
ucgauaucaa gcuuaucgau accgucgaac ucgaggggggg gcccgguacc cagcuuuugu  120
ucccuuuagu gaggguuaau ugcgcgcuug gcguaaucau ggucauagcu guuuccugug  180
ugaaauuguu auccgcucac aauuccacac aacauacgag ccggauuuuu uucc        234

<210> SEQ ID NO 67
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 67
gggauccccc acaauccugu cguuaccugu cauguauccg ucuagauggg cugcaggaau    60
ucgauaucaa gcuuaucgau accgucgauc ucgaggggggg gcccgguacc cagcuuuugu  120
ucccuuuagu gaggguuaau ugcgcgcuug gcguaaucau ggucauagcu guuuccugug  180
ugaaauuguu auccgcucac aauuccacac aacauacgag ccggauuuuu uucc        234

<210> SEQ ID NO 68
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 68
gggauccccc acaauccugu cguuaccugu cauguauccg ucuagauggg cugcaggaau    60
ucgauaucaa gcuuaucgau accgucgacg ucgaggggggg gcccgguacc cagcuuuugu  120
ucccuuuagu gaggguuaau ugcgcgcuug gcguaaucau ggucauagcu guuuccugug  180
ugaaauuguu auccgcucac aauuccacac aacauacgag ccggauuuuu uucc        234

<210> SEQ ID NO 69
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 69
gggauccccc acaauccugu cguuaccugu cauguauccg ucuagauggg cugcaggaau    60
ucgauaucaa gcuuaucgau accgucgaca ucgaggggggg gcccgguacc cagcuuuugu  120
ucccuuuagu gaggguuaau ugcgcgcuug gcguaaucau ggucauagcu guuuccugug  180
ugaaauuguu auccgcucac aauuccacac aacauacgag ccggauuuuu uucc        234

<210> SEQ ID NO 70
<211> LENGTH: 234
<212> TYPE: RNA
<213> ORGANISM: Artificial Sequence

```
<220> FEATURE:
<223> OTHER INFORMATION: Description of Artificial Sequence: Synthetic
      dsRNA substrate sequence

<400> SEQUENCE: 70 gggaucccce acaauccugu cguuaccugu cauguauccg ucuagauggg cugcaggaau      60
ucgauaucaa gcuuaucgau accgucgacu ucgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234

<210> SEQ ID NO 71
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 71 gggaucccce acaauccugu cguuaccugu cauguauccg ucuagauggg cugcaggaau      60
ucgauaucaa gcuuaucgau accgucgacc gcgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234

<210> SEQ ID NO 72
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 72 gggaucccce acaauccugu cguuaccugu cauguauccg ucuagauggg cugcaggaau      60
ucgauaucaa gcuuaucgau accgucgacc acgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234

<210> SEQ ID NO 73
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 73 gggaucccce acaauccugu cguuaccugu cauguauccg ucuagauggg cugcaggaau      60
ucgauaucaa gcuuaucgau accgucgacc ccgagggggg gcccgguacc cagcuuuugu    120
ucccuuuagu gaggguuaau ugcgcgcuug gcguaaucau ggucauagcu guuuccugug    180
ugaaauuguu auccgcucac aauuccacac aacauacgag ccggauuuuu uucc          234

<210> SEQ ID NO 74
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence
```

<400> SEQUENCE: 74 gggaucccccc acaauccugu cguuaccugu cauguauccg ucuagauggg cugcaggaau    60
ucgauaucaa gcuuaucgau accgucgacc uggaggggggg gcccgguacc cagcuuuugu   120
ucccuuuagu gagggguuaau ugcgcgcuug gcguaaucau ggucauagcu guuuccugug   180
ugaaauuguu auccgcucac aauuccacac aacauacgag ccggauuuuu uucc          234

<210> SEQ ID NO 75
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 75 gggaucccccc acaauccugu cguuaccugu cauguauccg ucuagauggg cugcaggaau    60
ucgauaucaa gcuuaucgau accgucgacc uagaggggggg gcccgguacc cagcuuuugu   120
ucccuuuagu gagggguuaau ugcgcgcuug gcguaaucau ggucauagcu guuuccugug   180
ugaaauuguu auccgcucac aauuccacac aacauacgag ccggauuuuu uucc          234

<210> SEQ ID NO 76
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 76 gggaucccccc acaauccugu cguuaccugu cauguauccg ucuagauggg cugcaggaau    60
ucgauaucaa gcuuaucgau accgucgacc uugaggggggg gcccgguacc cagcuuuugu   120
ucccuuuagu gagggguuaau ugcgcgcuug gcguaaucau ggucauagcu guuuccugug   180
ugaaauuguu auccgcucac aauuccacac aacauacgag ccggauuuuu uucc          234

<210> SEQ ID NO 77
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 77 gggaucccccc acaauccugu cguuaccugu cauguauccg ucuagauggg cugcaggaau    60
ucgauaucaa gcuuaucgau accgucgacc ucaggggggg gcccgguacc cagcuuuugu    120
ucccuuuagu gagggguuaau ugcgcgcuug gcguaaucau ggucauagcu guuuccugug   180
ugaaauuguu auccgcucac aauuccacac aacauacgag ccggauuuuu uucc          234

<210> SEQ ID NO 78
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 78

```
gggaucccccc acaauccugu cguuaccugu cauguauccg ucuagaugggg cugcaggaau    60 ucgauaucaa gcuuaucgau accgucgacc ucuaggggg gcccgguacc cagcuuuugu      120
ucccuuuagu gagggguaau ugcgcgcuug gcguaaucau ggucauagcu guuccugug      180 ugaaauuguu auccgcucac aauuccacac aacauacgag ccggauuuuu uucc           234
```

<210> SEQ ID NO 79  
<211> LENGTH: 234  
<212> TYPE: RNA  
<213> ORGANISM: Artificial Sequence  
<220> FEATURE:  
<223> OTHER INFORMATION: Description of Artificial Sequence: Synthetic  
     dsRNA substrate sequence <400> SEQUENCE: 79

```
gggaucccccc acaauccugu cguuaccugu cauguauccg ucuagauggg cugcaggaau    60
ucgauaucaa gcuuaucgau accgucgacc uccaggggggg gcccgguacc cagcuuuugu    120
ucccuuuagu gagggguaau ugcgcgcuug gcguaaucau ggucauagcu guuccugug      180 ugaaauuguu auccgcucac aauuccacac aacauacgag ccggauuuuu uucc           234
```

<210> SEQ ID NO 80  
<211> LENGTH: 234  
<212> TYPE: RNA  
<213> ORGANISM: Artificial Sequence  
<220> FEATURE:  
<223> OTHER INFORMATION: Description of Artificial Sequence: Synthetic  
     dsRNA substrate sequence <400> SEQUENCE: 80

```
gggaucccccc acaauccugu cguuaccugu cauguauccg ucuagauggg cugcaggaau    60
ucgauaucaa gcuuaucgau accgucgacc ucgggggggg gcccgguacc cagcuuuugu     120
ucccuuuagu gagggguaau ugcgcgcuug gcguaaucau ggucauagcu guuccugug      180 ugaaauuguu auccgcucac aauuccacac aacauacgag ccggauuuuu uucc           234
```

<210> SEQ ID NO 81  
<211> LENGTH: 234  
<212> TYPE: RNA  
<213> ORGANISM: Artificial Sequence  
<220> FEATURE:  
<223> OTHER INFORMATION: Description of Artificial Sequence: Synthetic  
     dsRNA substrate sequence <400> SEQUENCE: 81

```
gggaucccccc acaauccugu cguuaccugu cauguauccg ucuagauggg cugcaggaau    60
ucgauaucaa gcuuaucgau accgucgacc ucguggggg gcccgguacc cagcuuuugu      120
ucccuuuagu gagggguaau ugcgcgcuug gcguaaucau ggucauagcu guuccugug      180 ugaaauuguu auccgcucac aauuccacac aacauacgag ccggauuuuu uucc           234
```

<210> SEQ ID NO 82  
<211> LENGTH: 234  
<212> TYPE: RNA  
<213> ORGANISM: Artificial Sequence  
<220> FEATURE:  
<223> OTHER INFORMATION: Description of Artificial Sequence: Synthetic  
     dsRNA substrate sequence <400> SEQUENCE: 82

```
gggaucccccc acaauccugu cguuaccugu cauguauccg ucuagauggg cugcaggaau    60
ucgauaucaa gcuuaucgau accgucgacc ucgcggggg gcccgguacc cagcuuuugu      120
```
ucccuuuagu gaggguuaau ugcgcgcuug gcguaaucau ggucauagcu guuccugug    180 ugaaauuguu auccgcucac aauuccacac aacauacgag ccggauuuuu uucc         234

<210> SEQ ID NO 83
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 83
gggauccccc acaauccugu cguuaccugu cauguauccg ucuagauggg cugcaggaau    60
ucgauaucaa gcuuaucgau accgucgacc ucgaaggggg gcccgguacc cagcuuuugu   120
ucccuuuagu gaggguuaau ugcgcgcuug gcguaaucau ggucauagcu guuccugug    180 ugaaauuguu auccgcucac aauuccacac aacauacgag ccggauuuuu uucc         234

<210> SEQ ID NO 84
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 84
gggauccccc acaauccugu cguuaccugu cauguauccg ucuagauggg cugcaggaau    60
ucgauaucaa gcuuaucgau accgucgacc ucgauggggg gcccgguacc cagcuuuugu   120
ucccuuuagu gaggguuaau ugcgcgcuug gcguaaucau ggucauagcu guuccugug    180 ugaaauuguu auccgcucac aauuccacac aacauacgag ccggauuuuu uucc         234

<210> SEQ ID NO 85
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 85
gggauccccc acaauccugu cguuaccugu cauguauccg ucuagauggg cugcaggaau    60
ucgauaucaa gcuuaucgau accgucgacc ucgacggggg gcccgguacc cagcuuuugu   120
ucccuuuagu gaggguuaau ugcgcgcuug gcguaaucau ggucauagcu guuccugug    180 ugaaauuguu auccgcucac aauuccacac aacauacgag ccggauuuuu uucc         234

<210> SEQ ID NO 86
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 86
gggauccccc acaauccugu cguuaccugu cauguauccg ucuagauggg cugcaggaau    60
ucgauaucaa gcuuaucgau accgucgacc ucgagagggg gcccgguacc cagcuuuugu   120
ucccuuuagu gaggguuaau ugcgcgcuug gcguaaucau ggucauagcu guuccugug    180

-continued ugaaauuguu auccgcucac aauuccacac aacauacgag ccggauuuuu uucc        234

<210> SEQ ID NO 87
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 87 gggaucccccc acaauccugu cguuaccugu cauguauccg ucuagauggg cugcaggaau        60
ucgauaucaa gcuuaucgau accgucgacc ucgagugggg gcccgguacc cagcuuuugu       120
ucccuuuagu gagggguuaau ugcgcgcuug gcguaaucau ggucauagcu guuccugug       180 ugaaauuguu auccgcucac aauuccacac aacauacgag ccggauuuuu uucc        234

<210> SEQ ID NO 88
<211> LENGTH: 234
<212> TYPE: RNA
<213> ORGANISM: Artificial Sequence
<220> FEATURE:
<223> OTHER INFORMATION: Description of Artificial Sequence: Synthetic
      dsRNA substrate sequence

<400> SEQUENCE: 88
gggauccccc acaauccugu cguuaccugu cauguauccg ucuagauggg cugcaggaau        60
ucgauaucaa gcuuaucgau accgucgacc ucgagcgggg gcccgguacc cagcuuuugu       120
ucccuuuagu gagggguuaau ugcgcgcuug gcguaaucau ggucauagcu guuccugug       180 ugaaauuguu auccgcucac aauuccacac aacauacgag ccggauuuuu uucc        234

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccagaggcag aaatgccaag tc        22

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccagcaccgc ttcctcttc        19

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ccggcagaaa tgccaagtca gg        22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ccttcagcac cgcttcctct tc                                        22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ccaatgccaa gtcagggaca ac                                        22

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cgcctctttt cagcaccgc                                            19

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctgccaagtc agggacaac                                            19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctctgcctct tttcagcac                                            19

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cctcagggac aacacctaaa aatacag                                   27

```
<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccgcatttct gcctcttttc agc                                               23

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ctgggacaac acctaaaaat ac                                                22

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctttggcatt tctgcctc                                                     18

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ccacacctaa aaatacagat gttc                                              24

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cgcctgactt ggcatttc                                                     18

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ccaatacaga tgttcagacg taccg                                             25

<210> SEQ ID NO 104
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ccggtgttgt ccctgacttg                                                 20

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cacagatgtt cagacgtacc g                                               21

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gccttaggtg ttgtccctg                                                  19

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ccgttcagac gtaccgctac                                                 20

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ccgtattttt aggtgttgtc cctg                                            24

<210> SEQ ID NO 109
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cgtgttcaga cgtaccgcta cagtacag                                        28

<210> SEQ ID NO 110
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110 tgtatttttta ggtgttgtcc ctgacttg                                     28

<210> SEQ ID NO 111
<211> LENGTH: 7
<212> TYPE: RNA
<213> ORGANISM: Artificial Sequence
<220> FEATURE:
<223> OTHER INFORMATION: Description of Artificial Sequence: Synthetic
      consensus sequence

<400> SEQUENCE: 111 daccuhd                                                              7

<210> SEQ ID NO 112
<211> LENGTH: 11
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (9)..(10)
<223> OTHER INFORMATION: a, c, u, g, unknown or other

<400> SEQUENCE: 112
ygaccucgnn g                                                        11

<210> SEQ ID NO 113
<211> LENGTH: 14
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (12)..(13)
<223> OTHER INFORMATION: a, c, u, g, unknown or other

<400> SEQUENCE: 113
nnnygaccuc gnng                                                     14

<210> SEQ ID NO 114
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gcuauggcag cuggagcucc cccccgggcc                                    30

<210> SEQ ID NO 115
<211> LENGTH: 18
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 115
ggagcucccc cccgggcc                                                  18

<210> SEQ ID NO 116
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gagcuccccc ccgggcc                                                   17

<210> SEQ ID NO 117
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117 agcuccccccc cgggcc                                                   16

<210> SEQ ID NO 118
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
cgauaccguc gacc                                                      14

<210> SEQ ID NO 119
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cgauaccguc gac                                                       13

<210> SEQ ID NO 120
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
cgauaccguc ga                                                        12

<210> SEQ ID NO 121
<211> LENGTH: 7
<212> TYPE: RNA
<213> ORGANISM: Artificial Sequence
<220> FEATURE:

-continued

```
<223> OTHER INFORMATION: Description of Artificial Sequence: Synthetic
      consensus sequence

<400> SEQUENCE: 121 hdagguh                                                                    7

<210> SEQ ID NO 122
<211> LENGTH: 11
<212> TYPE: RNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (2)..(3)
<223> OTHER INFORMATION: a, c, u or g

<400> SEQUENCE: 122
cnncgagguc r                                                              11
```